(12) United States Patent
Ranby

(10) Patent No.: US 10,613,104 B2
(45) Date of Patent: Apr. 7, 2020

(54) ASSAY TO DETERMINE ANTICOAGULANTS IN BLOOD OR BLOOD PLASMA

(71) Applicant: ZAFENA AB, Borensberg (SE)

(72) Inventor: Mats Ranby, Vreta Kloster (SE)

(73) Assignee: ZAFENA AB, Borensberg (SE)

( * ) Notice: Subject to any disclaimer, the term of this patent is extended or adjusted under 35 U.S.C. 154(b) by 0 days.

(21) Appl. No.: 15/311,255

(22) PCT Filed: May 21, 2015

(86) PCT No.: PCT/EP2015/061292
§ 371 (c)(1),
(2) Date: Nov. 15, 2016

(87) PCT Pub. No.: WO2015/177293
PCT Pub. Date: Nov. 26, 2015

(65) Prior Publication Data
US 2017/0089932 A1    Mar. 30, 2017

(30) Foreign Application Priority Data
May 22, 2014  (SE) ....................... 1450612

(51) Int. Cl.
*G01N 33/86* (2006.01)
*C12Q 1/56* (2006.01)
(52) U.S. Cl.
CPC ............. *G01N 33/86* (2013.01); *C12Q 1/56* (2013.01)
(58) Field of Classification Search
CPC ..................................................... G01N 33/86
(Continued)

(56) References Cited

U.S. PATENT DOCUMENTS 3,650,698 A * 3/1972 Adler ................... B01F 13/0809
210/222
4,149,405 A * 4/1979 Ringrose ................. G01N 11/00
356/39

(Continued)

FOREIGN PATENT DOCUMENTS

| EP | 2405274 A1 | 1/2012 |
|---|---|---|
| EP | 2722674 A1 | 4/2014 |
| WO | 2006/100346 A1 | 9/2006 |

OTHER PUBLICATIONS

Hemker, H. C. et al, Nature 1963, 200, 589-590.*

(Continued)

*Primary Examiner* — Arlen Soderquist
(74) *Attorney, Agent, or Firm* — Olive Law Group, PLLC; Tristan A. Fuierer

(57) ABSTRACT

An assay to determine anticoagulants in a blood or blood plasma sample, wherein the assay comprises analyses with at least two wet chemistry prothrombine time (PT) methods. The assay comprises measuring PT in a first reaction mixture with a first PT method and measuring PT in a second reaction mixture with a second PT method, wherein the concentration of blood or blood plasma in the second reaction mixture differs from the concentration of blood or blood plasma in the first reaction mixture. The PT methods are calibrated to give the same or approximately the same PT results for reference samples which lack anticoagulants of interest for the assay. Further, calculating a difference in PT from the measurements, wherein if the difference in PT is 1) significant, this is indicative of a presence of anticoagulants in the sample, or 2) non-significant, this is indicative of an absence of anti-coagulants above detectable level in the sample.

15 Claims, 8 Drawing Sheets

(58) Field of Classification Search
USPC .............................................. 422/73; 436/69
See application file for complete search history.

(56) References Cited

U.S. PATENT DOCUMENTS

| | | | | |
|---|---|---|---|---|
| 4,289,498 | A | * | 9/1981 | Baughman ............... C12Q 1/56 436/164 |
| 4,784,944 | A | * | 11/1988 | Kolde .................... G01N 33/86 435/13 |
| 5,221,614 | A | | 6/1993 | Enomoto |
| 5,525,477 | A | * | 6/1996 | Hassouna ................ C12Q 1/56 435/13 |
| 5,705,395 | A | * | 1/1998 | Griffin ................... G01N 33/86 422/504 |
| 5,981,285 | A | * | 11/1999 | Carroll ............... G01N 33/4905 422/73 |
| 5,994,140 | A | * | 11/1999 | Speck ..................... C12Q 1/56 435/13 |
| 7,745,224 | B2 | * | 6/2010 | Zander ................... G01N 33/86 435/13 |
| 7,767,459 | B2 | | 8/2010 | Horsti |
| 8,759,094 | B2 | * | 6/2014 | Ranby .................. G01N 33/491 435/366 |
| 9,234,902 | B2 | * | 1/2016 | Onundarson .......... G01N 33/86 |
| 2003/0064414 | A1 | * | 4/2003 | Benecky .................. C12Q 1/56 435/7.21 |
| 2005/0136499 | A1 | * | 6/2005 | Henckel ................ G01N 33/86 435/13 |
| 2005/0260696 | A1 | * | 11/2005 | Griffin ................... G01N 33/86 435/13 |
| 2006/0281140 | A1 | * | 12/2006 | Ranby ................ G01N 33/4905 435/13 |
| 2007/0020765 | A1 | * | 1/2007 | Zander ................... G01N 33/86 436/69 |
| 2008/0318259 | A1 | * | 12/2008 | Ranby .................. G01N 33/491 435/13 |
| 2009/0263903 | A1 | * | 10/2009 | Horsti ..................... C12Q 1/56 436/43 |
| 2012/0231485 | A1 | * | 9/2012 | Onundarson .......... G01N 33/86 435/13 |
| 2012/0309035 | A1 | * | 12/2012 | Lindahl ................ A61K 9/0019 435/13 |

OTHER PUBLICATIONS

Hemker, H. C. et al, Thrombsis et Diathesis Haemorrhagica 1967, 17, 349-357.*
Hemker, H. C. et al, Thrombsis et Diathesis Haemorrhagica 1968, 19, 368-382.*
Furie, B. et al, Blood 1984, 64, 445-451.*
Lawrie, A. S. et al, British Journal of Haemtology 1997, 98, 887-892.*
Weinstock, D. M. et al, American Journal of Hematology 1998, 57, 193-199.*
McGlasson, D. L., Laboratory Medicine 2003, 34, 124-129.*
Tobu, M. et al, Clinical and Applied Thrombosis/Hemostasis 2003, 10, 301-309.*
Horsti, J. et al, Clinical Chemistry 2005, 51, 553-560.*
Horsti, J. et al, The Open Medicinal Chemistry Journal 2008, 2, 11-15.*
Horsti, J. et al, The Open Hematology Journal 2008, 2, 81-85.*
Carreiro, J. et al, Expert Opinion on Investigational Drugs 2008, 17, 1937-1945.*
Wong, P. C. et al, Journal of Thrombosis and Haemostasis 2009, 7, 1313-1320.*
Horsti, J., Hematology Reviews 2009, paper 1:e15, 87-91.*
Van Ryn, J. et al, Thrombosis and Haemostasis 2010, 103, 1116-1127.*
Barrett, Y. C. et al, Thrombosis and Haemostasis 2010, 104, 1263-1271.*
Gudmundsdottir, B. R. et al, Thrombosis Research 2012, 130, 674-681.*
Duffull, S. B. et al, New Zealand Medical Journal 2012, 125, 148-154.*
Douxfils, J. et al, Thrombosis and Haemostasis 2010, 107, 1-13.*
Funk, D. M., Hematology 2012, 460-465.*
Yeo, C. H. et al, American Medical Journal 2012, 3, 126-129.*
Van Ryn, J. et al, The American Journal of Medicine 2012, 125, 417-420.*
Wychowski, M. K. et al, Annals of Pharacotherapy 2012, 46, 608.*
Miyarees, M. A. et al, American Journal of Health-System Pharmacists 2012, 69, e28-e39.*
Dager, W. E. et al, Annals of Pharacotherapy 2012, 46, 1627-1636.*
Barrett, Y. C. et al, Clinical and Applied Thrombosis/Hemostasis 2013, 19, 522-528.*
Douxfils, J. et al, Thrombosis and Haemostasis 2013, 110, 283-294.*
Hawes, E. M. et al, Journal of Thrombosis and Haemostasis 2013, 11, 1493-1502.*
Kim, J. et al, Case Reports in Medicine 2013, Article 131395, 4 pages.*
Ciurus, T. et al, Kardiochirurgia i Torakochirurgia Polska 2015, 12, 111-118.*
Hemker, H. C. et al, Thrombosis et Diathesis Haemorrhagica 1968, 20, 78-87.*
Jonsson, M. et al, Thrombosis Research 2004, 114, 83-89.*
Jackson, C. M. et al, Clinical Chemistry 2005, 51, 483-485.*
Bates, S. M. et al, Circulation 2005, 112, e53-e60.*
Castellone, D. D. et al, American Journal of Hematology 2010, 85, 185-187.*
Hillarp, A. et al, Journal of Thrombosis and Haemostasis 2010, 9, 133*139.*
Lindahl, T. L. et al, Thrombosis and Haemostasis 2011, 105, 371+378.*
Halbmayer, W.-M. et al, Clinical Chemistry and Laboratory Medicine 2012, 50, 1601-1605.*
Miyares, M. A. et al, American Journal of Health-System Pharmacists 2012, 69,1473-1484.*
Gerotziafas, G. T. et al, Thrombosis Research 2012, 129, 101-103.*
Douxfils, J. et al, Thrombosis Research 2012, 130, 956-966 and 20 pages of supplementary material.*
Eby, C., International Journal of Laboratory Hematology 2013, 35, 262-268.*
Baglin, T. et al, Journal of Thrombosis and Haemostasis 2013, 11, 756-760.*
Di Minno, A. et al, Seminars in Thrombosis and Hemostasis 2013, 39, 840-846.*
Owren, P. A., Lancet 1959, 274, 754-758.*
Ware, A. G. et al, Angiology 1964, 15, 11-16.*
Gomperts, E. D. et al, Thrombosis Research 1977, 12, 105-117.*
Pieters, J. et al, Blood 1989, 74, 1021-1024.*
Kasper, C. K., Blood Coagulation and Fibrinolysis 1991, 2, Supplement 1, 7-10.*
Hemker, H. C. et al, Haemostaslis 1991, 21, 258-272.*
Triplett, D. A., Lupus 1994, 3, 281-287.*
Alhenc-Gelas, M. et al, Nephron 1995, 71, 149-152.*
Samama, M. M. Thombosis and Hemostasis 1995, 15, 119-121.*
Kessler, C. M. et al, American Journal of Clinical Pathology 1995, 103, 642-648.*
Massicotte, P. et al, Journal of Pidiatrics 1996, 128, 13-18.*
Abbate, R. et al, American Journal of Cardiology 1998, 82, 33L-36L.*
Kitchen, S. et al, Seminars in Thrombosis and Hemostasis 1999, 25, 17-26.*
Rozanski, E. A. et al, Journal of veternary Emergency and Critical Care 1999, 9, 73-78.*
Crowther, M. A. et al, Thrombosis Research 2000, 98, 133-138.*
Bombeli, T. et al, Haemostasis 2001, 31, 90-98.*
Fenyvesi, T. et al, Clinical Chemistry2002, 48, 1791-1794.*
Testa, S. et al, Haematologica 2002, 87, 1265-1273.*
Mount, M. E. et al, Journal of the American Veterinary Medical Association 2003, 222, 194-198.*
Wienen, W. et al, Thrombosis and Haemostasis 2007, 98, 155-162.*

(56) References Cited

OTHER PUBLICATIONS

Kamal, A. F. et al, Mayo Clinic Proceedings 2007, 82, 864-873.*
Gray, E. et al, "Monitoring new anticoagulants" in Quality in Laboratory Hemostasis and Thrombosis, 2009, Kitchen, S. et al, Ed., 190-197.*
Verbruggen, B. et al, "Detecting and quantifying functional inhibitors in hemostasis" in Quality in Laboratory Hemostasis and Thrombosis, 2009, Kitchen, S. et al, Ed., 198-207.*
Freyburger, G. et al, Thrombosis Research 2011, 127, 457-465.*
Mani, H. et al, Thrombosis and Haemostasis 2011, 106, 156-164.*
Harenberg, J. et al, Blood Coagulation and Fibrinolysis 2011, 22, 637-641.*
Harenberg, J. et al, Seminars in Thrombosis and Hemostasis 2012, 38, 16-22.*
Douxfils, J. et al, Thrombosis and Haemostasis 2012, 107, 985-997.*
Curvers, J. et al, American Journal of Clinical Pathology 2012, 138, 551-558.*
Jones, S. D. F. et al, Pathology 2012, 44, 578-580.*
Helin, T. A. et al, Clinical Chemistry 2013, 59, 807-814.*
Patel, J. P. et al, British Journal of Haematology, 2013, 162, 706-718.*
Antovic, J. P. et al, European Journal of Clinical Pharmacology 2013, 69, 1875-1881.*
Olah, Z. et al, Archives of Pathology & Laboratory Medicine 2013, 137, 967-973.*
Rodgers, R. et al, British Journal of Haematology, 2013, 163, 674-687.*
Wool, G. D. et al, American Journal of Clinical Pathology 2013, 140, 623-634.*
Conversy, B. et al, The Veterinary Journal 2013, 198, 437-443.*
Kitchen, S. et al, British Journal of Haematology 2014, 166, 830-841.*
Tomas Lindahl, et al; "INR calibration of Owren-type prothrombin time based on the relationship between PT% and INR utilizing normal plasma samples." Thrombosis and Haemostasis. Apr. 5, 2004. pp. 1225-1226. DOI: 10.1160/TH03-07-0456.
Meyer Michel Samama, et al; "Assessment of laboratory assays to measure rivaroxaban—an oral, direct factor Xa inhibitor." Thrombosis and Haemostasis. Apr. 1, 2010. pp. 815-825. vol. 103, No. 4. Schattauer GMBH, DE.
Chaoho Ouyang, et al; "Purification and properties of the anticoagulant principle of Trimeresurus gramineus venom." BBA—Protein Structure. Apr. 29, 1975. pp. 479-492. vol. 386, No. 2. Elsevier Scientific Publishing Company. Amsterdam, NL.
Borensberg; "ZAFENA The Simple Simon concept. The product Simple Simon PT." Nov. 17, 2008. http://www.zafena.se/uploads/English/SSPTHandoutEngnov-08.pdf.
International Search Report and Written Opinion for PCT/EP2015/061292 dated Jul. 14, 2015.
A. Tripodi, et al; "The International Normalized Ratio calibrated for rivaroxaban has the potential to normalize prothrombin time results for rivaroxaban-treated patients: results of an in vitro study." J Thromb Haemost 2011; 9: 226-8.
Swedish Office action dated Nov. 25, 2014 from related Swedish Application No. 1450612-5.
Swedish Office action dated Apr. 22, 2016 from related Swedish Application No. 1450612-5.
Swedish Office action dated Dec. 27, 2016 from related Swedish Application No. 1450612-5.
Chinese-language Office Action issued in counterpart Chinese Application No. CN 201580027220.6 dated Nov. 30, 2017 with English translation (four (4) pages).
European Communication pursuant to Article 94(3) EPC issued in counterpart Application No. EP 15726897.0 dated Oct. 20, 2017 (five (5) pages).

* cited by examiner

ASSAY TO DETERMINE ANTICOAGULANTS IN BLOOD OR BLOOD PLASMA

CROSS REFERENCE TO RELATED APPLICATIONS

This application is a 35 USC 371 application of International PCT Patent Application No. PCT/EP2015/061292, filed on May 21, 2015, which claims priority to Sweden Patent Application No. 1450612-5, filed on May 22, 2014; the contents of which are hereby incorporated by reference herein in their entireties.

TECHNICAL FIELD

The present disclosure relates to an assay to determine anticoagulants in a blood or blood plasma sample.

BACKGROUND

Anticoagulants are substances that dampen, reduce or abolish the ability of blood, or blood plasma, to coagulate—anticoagulants reduce the rate by which the fibrinogen is converted into fibrin.

Some anticoagulants are naturally occurring, endogenous, and play important physiological roles in limiting the onset, the speed of propagation and the spatial extension of blood coagulation in vivo. Other anticoagulants appear under pathological conditions. There are anticoagulants found in snake-toxins and in excretions of mosquitoes, leaches, bats and ticks. A growing group of anticoagulants are man-made substances created for the purposes of treating and preventing thromboembolic disorders.

Blood coagulation is a complex phenomenon involving a multitude of interacting molecules found in blood plasma or on the surface of engaged cells. There are numerous cellular and molecular interactions, including many enzymatically catalyzed reactions, which may be down-regulated or disrupted, by the action of anticoagulants.

The direct acting anticoagulants inhibit, hamper or abolish the enzymatic activity of one or both of the critical enzymes in the coagulation process, thrombin (FIIa) or activated coagulation factor X (FXa). Indirect acting anticoagulants work in some other way, one of which is to enhance the potency of direct acting inhibitors. Of anticoagulants in general therapeutic use, heparin is an indirect acting anticoagulant and the vitamin-K antagonists (warfarin) are general reducers of coagulation factor levels. Direct acting anticoagulants are hirudin (a protein of the leach) and the recently created inhibitors of FIIa or FXa. It is these new direct acting anticoagulants, particularly those that can be administered orally, DOACs or as also called NOACs (Non-Vitamin K Oral Anticoagulants), that are causing a profound change within clinical, and laboratory medicine.

The fact that anticoagulants have different modes of action poses a challenge to laboratory medicine in devising methods by which the anticoagulants can be determined. To a degree, this challenge is exasperated by recent pharmacological successes in creating new substances to treat thromboembolic disorders, see e.g. J. Harenburg, S. Marx and R. Kramer, Determination of the anticoagulation effects of the new oral anticoagulants: an unmet need, Expert Review of Haematology, February 2012, Vol. 5, No. 1, Pages 107-113.

At central hospital laboratories, where there is a variety of tests available and qualified personnel to interpret the results, detection and determination of the DOAC appears relatively straightforward—the FIIa inhibitors and FXa inhibitors may be assayed by thrombin time (TT) tests or the FXa tests, respectively. If standard variants of these tests do not fulfill the needs, some modification or "dilution" of the standard variants will. At primary care centers, and at places, sites, within hospitals but remote from the central laboratory, "off-site", the situation is different. Characteristic for laboratory medicine at POC-sites (Point of Care) is that the number of different laboratory tests is limited because the physical space of such laboratory sites is limited and because the availability of qualified laboratory personnel is limited. Within coagulation the most available POC test is the prothrombin test (PT-test) with the results expressed in INR (international normalized ratio, a ratio between the PT of the sample and a normal PT normalized by being powered to normalizing exponent, a sensitivity index). Other "routine" or "common" coagulation test are activated partial thromboplastin time (APTT), activated coagulation time (ACT) and the mentioned TT. It is the hope of visionary experts in the coagulation field that these "routine" or "common" coagulation tests can be adapted, modified, "diluted", to fulfill the POC need in assaying the "new" anticoagulants, particularly the NOAC. Such thoughts/hopes are for example expressed by E. J. Favaloro and G. Lippi, The new oral anticoagulants and the future of haemostasis laboratory testing, Biochemia Medica 2012; 22(3):329-41.

Because PT-INR is the most commonly available POC-test for coagulation measurements, a modified PT-test or "diluted PT" by which the NOAC can be determined is highly desirable. There is reported work in such direction. The low sensitivity of most PT-tests for direct FXa inhibitors, such as rivaroxaban, is known. C. Kluft discloses in EP 2 405 274 A1 that PT-tests that are affected by a certain snake venom, RVV-V, also show sensitivity toward rivaroxaban, and discloses the use of a PT-test that employ such thromboplastins.

The hopes of finding a way to determine NOAC by some PT-test, modified or not, has during the recent years declined. In January of 2014, T. Lindahl, a member of expert group in coagulation of the external quality organization of Sweden, EQUALIS, reported on studies performed by the expert group on one FXa-inhibiting substance aprixaban. The conclusion was that none of the many commercially available PT or APTT tests was of use in determining aprixaban at clinically relevant concentrations in blood plasma. FXa-tests, on the other hand worked well for this purpose.

Efforts to correct PT-results for the variable anticoagulant effect of non-functioning coagulation factors, pivka, found in the blood of patients on treatments with vitamin-K antagonists, warrant to be mentioned. U.S. Pat. No. 7,767,459 B2 (J. Horsti) provides for this by measuring PT of blood plasma by the standard protocol of any given PT method, and also measuring the same after a pre-dilution of the plasma with a physiological buffer such as 9 g/l NaCl. The PT results, expressed either in seconds or in INR, are then plotted against the degree of final plasma dilution and extrapolated to zero. The PT of the plasma at final dilution of zero, reduced by the same for a normal plasma, is taken as a measure of the pivka-effect and is used to correct the original PT-result.

New coagulation tests have been devised with the aim to determine several different kinds of anticoagulants, particularly heparins and NOACs.

These efforts demonstrate the clinical importance of determining these anticoagulants.

See Calatzis A, Peletz D, Haas S, Spannagl M, Rudin K, Wilmer M, Prothromibnase-induced Clotting Time Assay for Determination of the Anticoagulant Effects of UFH and LMWH, Fondaparinux, and Thrombin Inhibitors, Am J Clin Pathol 2008; 130: 446-454, and Samama M M, Martinoli J L, LeFlem L, Guinet C, Plu-Bureau G, Depasse F, Assessment of laboratory assays to measure rivaroxaban—an oral, direct factor Xa inhibitor, Thromb Haemost 2010; 103/4: 815-825.

Relevant background to the present invention is the distinction between wet-chemistry methods and dry chemistry methods. Wet-chemistry is defined by the mixing of a volume of the sample, in a coagulation assay of blood or blood plasma, and a volume of reagent. The sample is thus diluted to a certain degree in the reaction mixture. In dry-chemistry this dilution does not occur. The sample is mixed, or contacted, with reagent substance in a dry form and there is no dilution of the sample. Most POC-tests are dry-chemistry tests because they can often be presented in an easy to use format, e.g. a strip or a chip. The operator needs typically only to add a small volume of the sample. A disadvantage of dry-chemistry methods is that the tests are more difficult to modify. One dimension of the freedom granted by the wet-chemistry procedures, variation of the degree of sample dilution, is not available with dry-chemistry. Every mention of a "diluted" modification of a "routine" test has wet-chemistry as a prerequisite.

SUMMARY

It is an object of the present disclosure to provide an assay to determine anticoagulants in a blood or blood plasma sample, the assay involving analyses with at least two wet chemistry prothrombine time (PT) methods, which assay is designed to be applicable for determination of both direct and indirect anticoagulants in blood or blood plasma samples.

The invention is defined by the appended independent claim. Embodiments are set forth in the dependent claims, in the attached drawings and in the following description.

According to a first aspect there is provided an assay to determine anticoagulants in a blood or blood plasma sample, wherein the assay comprises analyses with at least two wet chemistry prothrombine time (PT) methods. The assay comprises the steps of: a) in a first PT analysis with a first PT method measure PT in a first reaction mixture comprising a first volume of blood or blood plasma diluted in a first volume of a liquid reagent comprising thromboplastin, fibrinogen and coagulation factor V, b) in a second PT analysis with a second PT method measure PT in a second reaction mixture comprising a second volume of the blood or blood plasma diluted in a second volume of the liquid reagent, wherein the concentration of blood or blood plasma in the second reaction mixture differs from the concentration of blood or blood plasma in the first reaction mixture. The at least two PT methods are calibrated to give the same or approximately the same PT results when used to analyze reference blood or blood plasma which lack anticoagulants of interest for the assay. The assay further comprises the step of c) calculating a difference in PT from the measurements in step a) and b), wherein if the difference in PT is
1) significant, this is indicative of a presence of anticoagulants in the blood or blood plasma sample, or 2) non-significant, this is indicative of an absence of anti-coagulants above detectable level in the blood or blood plasma sample.

With analyses with at least two PT methods is here meant that the assay may involve analyses with 2, 3, 4, 5 or up to 6 PT methods.

With difference in PT is here meant absolute difference or relative difference.

The at least two PT methods used in the assay may be fundamentally the same PT method, but with some difference that may appear insignificant. Such differences, apart from the difference provided by the invention, i.e. difference in the relationship between sample volume and reagent volume, could be differences in the temperature at which the measurements are performed and differences in ionic strength or pH of the reaction mixture.

With wet chemistry PT method is here meant Owren type PT methods.

The ratio between the volume of blood or blood plasma and the volume of liquid reagent in the reaction mixture may vary widely depending on the characteristics of the PT reagent and the concentration in the sample of the anticoagulant to be detected.

When practicing the assay there are no strict limits to how little and how extensive the blood or blood plasma sample may be diluted in the PT reagent, the limits are of a practical nature. The lower level of blood or blood plasma sample dilution in a liquid reagent is about 1:2. At lower dilutions some favorable characteristics of the assay may be lost, e.g. citrated samples cease to be analyzable. The highest possible dilution will be considerably higher, about 1:200. Such high dilutions may be possible because necessary levels of fibrinogen and FV of the reaction mixture need not come from the sample. This is because liquid PT reagent of the Owren type, apart from thromboplastin, also contains effective levels of fibrinogen and FV. Still, also with liquid reagents of the Owren type there are practical limitations to the degree of final sample dilution. At very low levels of the blood or blood plasma sample in the reaction mixture, the levels of FVII, FX and FII are so low that the coagulation time (the PT) becomes so long that detection becomes difficult or impossible. Hence, in practicing the invention the ratio between the volume of blood or blood plasma and the volume of liquid reagent in the reaction mixture may be varied between 1:2 and 1:200. A preferred ratio range may be between 1:5 and 1:100 or between 1:10 and 1:50.

In the present assay, PT is analyzed in at least two reaction mixtures having different concentrations of blood or blood plasma in the reaction mixtures. The concentration of blood or blood plasma in the first reaction mixture may be about 1.5 to 100 times, 1.5 to 50 times, 1.5 to 25 times, 1.5 to 10 times or 1.5 to 5 times higher than the concentration of blood or blood plasma in the second reaction mixture. A difference in concentration of 1.5 to 5 times is practical to achieve and is with the present assay shown to allow determination of anticoagulants in clinically relevant concentration ranges.

The concentration of blood or blood plasma in the second reaction mixture may then be about 1.5 to 100 times, 1.5 to 50 times, 1.5 to 25 times, 1.5 to 10 times or 1.5 to 5 times higher than the concentration of blood or blood plasma in a possible third reaction mixture.

In spite of the difference in blood or blood plasma concentration in the reaction mixture, all the two or more different PT methods of the assay are calibrated to give, with relevant reference blood or blood plasma samples that lack the anticoagulant of interest, the same or approximately the same PT result. This PT is expressed in such a way that this is possible. Expression in regular time units will not do as these will vary from one method to another, and are what they are (cannot be calibrated). A reaction mixture with a low concentration of blood or blood plasma shows long PT:s and vice versa. A natural way to express PT is in INR (internationalized normalized ratio), but other expressions, various synthetic time-like units, or ratios of such, are possible. Important is that a given relevant sample lacking anticoagulant(s), analyzed by the two or more PT methods, will yield as closely as possible the same result. A natural way to compare the results from one PT method to another is by the average PT-result and by the CV (coefficient of variation) of the comparison. The calibration is such that the average PT-result for several relevant samples that lack the anticoagulant should be as nearly the same as possible with all of the two or more PT-methods, and the CV of the comparisons should be as low as possible.

The at least two PT methods may be calibrated such that the PT methods give the same or approximately the same PT result when used to analyze reference blood or blood plasma from a normal individual and dilutions of such reference blood or blood plasma. With blood or blood plasma from a normal individual is here meant blood or blood plasma, or pool(s) of such samples, from one or several apparently healthy person(s) not subject to anticoagulation treatment.

The at least two PT methods may be calibrated to give the same or approximately the same PT results when used to analyze blood or blood plasma (from a single or many individual(s) or pool of samples from different individuals) which lack anticoagulants of interest for the present assay and which blood or blood plasma has an above normal PT value determined by one or several established PT methods.

In step c) of the assay a difference, absolute or relative, in PT between PT measurements is calculated. The terms "significant" and "insignificant" are here given their conventional statistical definition. A significant difference is then a relative difference of 2 times CV or more, an insignificant difference less than 2 times CV. Differently expressed, an observed difference is significant if it has a low probability of occurring in a population of samples that lack the anticoagulants that are determined by the assay. This probability can be set at different levels. Typical levels are 5% ($p<0.05$), or 1% ($p<0.01$).

If the difference in PT calculated in step c) is significant and the identity of the anticoagulant is known, a concentration of the anticoagulant in the blood or blood plasma sample may be computed.

If the difference in PT calculated in step c) is non-significant and the identity of the anticoagulant is known, the level above which the anticoagulant is not present in said blood or blood plasma sample may be assigned.

If the difference in PT calculated in step c) is significant, an estimated PT of the blood or blood plasma sample in the absence of anticoagulants may be computable.

Computation of anticoagulant concentration in a blood or blood plasma sample can only be performed if the identity of the anticoagulant is known or assumed.

If analyses with two PT methods have been performed it may be expedient to use the difference in PT results and the PT-result from the analysis with the highest sample dilution for this calculation. The PT-result at the highest dilution will be closest to the PT-result should there be no anticoagulant present. Using the INR-formalism, this imagined PT-result is designated INRo. INRo may be obtained by subtracting a fraction of the difference, or subtracting a function of the difference, depending on if the dose-response to the anticoagulant level is linear or not. Since the dose-response may depend on this INRo and on the temperature at which the determinations have been made, the conversion of the size of the difference into anticoagulant concentration may require a multitude of so called standard curves. Alternatively a multidimensional function may be employed to compute INRo and the anticoagulant level.

If analyses with more than two PT-methods have been performed in practicing the assay of the invention, more than one difference can be computed, and these several differences, and the PT-value obtained at the highest sample dilution, can be used to compute the INRo and the possible anticoagulant levels depending on the identity of the anticoagulant. It is also possible to favor one of the differences as being most useable as it is a favorable range for the determinations.

The PT measurements may be performed at an ambient temperature in the range of 17° C. to 45° C., preferably in the range of 18° C. to 30° C., more preferably in the range of 21° C. to 30° C. and most preferably in the range of 25° C. to 30° C.

Such temperature intervals, lower than but not distant from 30° C., are favored since the temperature hardly affects the PT, thereby improving the precision of the provided PT analysis. In addition, a lower temperature increases the assay sensitivity for anticoagulants in the examples below.

The anticoagulants which may be determined in the present assay are members of a group comprising direct acting inhibitors of activated coagulation factors IIa and Xa, which may be selected from a group comprising dabigatran, apixaban, rivaroxaban or hirudin, or are members of a group comprising indirect acting inhibitors of activated coagulation factors IIa and Xa, which may be selected from a group comprising fractionated or unfractionated heparins.

The first volume of the liquid reagent in the first reaction mixture may be equal to the second volume of the liquid reagent in the second reaction mixture.

The volume of blood or blood plasma diluted in the liquid reagent may be in the range of 1 to 20 μL.

The volume of blood or blood plasma may be added to the liquid reagent with an end-to-end capillary.

The ratio between the volume blood or blood plasma and the volume of liquid reagent in the reaction mixture may be 1:2 to 1:200, 1:5 to 1:100 or 1:10 to 1:50.

A concentration of blood or blood plasma in the first reaction mixture may be about 1.5 to 100 times, 1.5 to 50 times, 1.5 to 25 times, 1.5 to 10 times or 1.5 to 5 times higher than the concentration of blood or blood plasma in the second reaction mixture.

The reaction mixture may comprise a final concentration of calcium ions in the range of 10 to 50 mM, in the range of 10 to 30 mM or in the range of 10 to 24 mM.

With final concentration of calcium in the reaction mixture is here meant the total calcium in the reaction mixture, mostly as free $Ca^{2+}$, but also complexed calcium ions.

With a reaction mixture comprising calcium of the stated concentrations the sensitivity by which coagulation inhibitors may be determined by the assay may be enhanced.

An excessively high calcium level should be avoided because increased $Ca^{2+}$ levels will progressively prolong the clotting times, which in general is disadvantageous.

The osmolarity of the reaction mixture may be about 0.3 to 0.5 Osm/kg, or about 0.3 to 0.4 Osm/kg.

Such osmolarity levels may be obtained by increasing the NaCl levels in the PT reagent to levels that make the PT reagent hypertonic (higher osmotic pressure than that of blood plasma and other physiological solutions), hence, also making the reaction mixture hypertonic.

Such osmolarity levels may increase the anticoagulant assay sensitivity. The clotting times may, however, become excessively long if the NaCl levels are too high.

A combination of increased osmolarity and increased calcium levels in the reaction mixture may increase the sensitivity of the anticoagulant assay to give the most advantageous high sensitivity.

DETAILED DESCRIPTION

Figure 1:
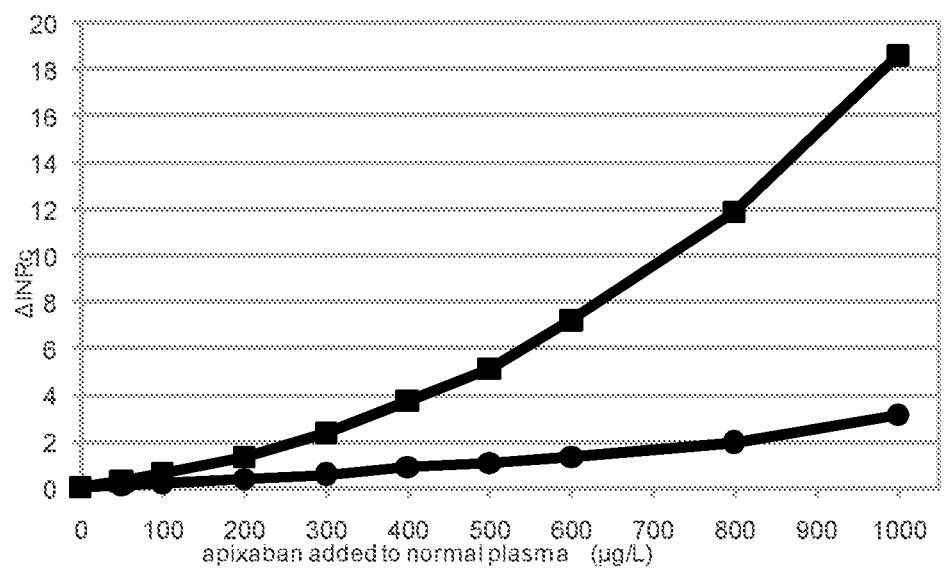
FIG. 1 is a graph showing apixaban content measured with the present assay in normal blood plasma.

Examples below are given, not to limit the scope of the invention, but to further explain and describe the invention, and to stimulate development in this important medical diagnostic area.

Experimental work was performed with the commercially available ambient room temperature coagulation instrument, Simple Simon P T Zafena A B, Linköping, Sweden, with functions described in EP 1 636 595 B2. One instrument or reader was used for each PT-method. Alternatively, the same instrument could be used for all PT-methods.

In Examples 1 to 6 one specific reader was used for each of the three PT methods, the 20 µL method, the 10 µL method and 5 µL method. The three instruments were used together standing next to one another on a laboratory bench in thermal equilibrium with the ambient room temperature of the laboratory. For a given PT determination each instrument displayed the PT in seconds, as reported on in Table 2. Also, via the internal data processing capacity of each reader, a rough estimate of the sample INR for each PT method was displayed. These rough INR estimates are reported on in Tables 1, 3 and 4. Since, in each series of experiments, relevant reference samples were also analyzed, the results from each PT-method could be calibrated in separate office desk session after the completion of an experimental series. No matter how the primary PT data of the two or more determinations by different PT methods is expressed, after the calibration using reference samples the different PT methods show, as closely as possible, the same PT.

The ambient room temperature in the laboratory where the work was done varied between 21° C. and 26° C. Temperature intervals lower than but not distant from 30° C. are favored since the temperature then hardly affects the PT, thereby improving the precision of the provided PT analysis. In addition, a lower temperature increases the assay sensitivity for anticoagulants in the examples below. The assay is, however, possible to perform at temperatures in the range of 17-45° C.

The PT-reagent was the one delivered together with lot N223M of the Simple Simon PT product, a reagent of Owren-type that thus contains effective amounts of thromboplastin, fibrinogen and FV (the thromboplastin of rabbit brain origin and the fibrinogen and the FV of bovine blood plasma origin). Other Owren type reagents could also be used.

The reagent was in portions of 200 µL to which sample, citrated blood or citrated blood plasma, was added and mixed. The addition was by an end-to-end plastic capillary mounted at one end of a tubular body with a displacement mechanism in the other end, this to allow convenient mixing of sample and reagent. Such Mixxocaps with 10 µL capillaries are supplied with the Simple Simon PT product. To perform the experiments described, some Mixxocaps were fitted with 20 µL capillaries, or 5 µL capillaries instead of the 10 µL capillaries with which they were supplied by the manufacturer. Alternatively, standard pipettes or similar may be used to mix the blood or blood plasma sample with the liquid reagent.

The ratios between the volume of blood or blood plasma to the volume of liquid reagent used in the experiments were 1:11, 1:21 and 1:41. Other ratios lying within the range of 1:5 and 1:100 or within the range of 1:2 and 1:200 could be used.

The difference in concentration of blood or blood plasma between the different reaction mixtures used in the assays in the experiments was between 1.5 to 5 times. The difference in concentration could, however, be about 1.5 times to 100 times.

Anticoagulated normal plasma was the NKP product GHI-163 lot 10188, MediRox AB, Nyköping, Sweden. Stock solutions of dabigatran (Pradaxa, Boehringer-Ingelheim) and apixaban (Eliquis, Bristol-Meyers Squibb) containing 100 mg/L were kind gifts of Professor Tomas Lindahl of the Department of Experimental Medicine of Linköping University. Unfractionated heparin was Heparin Leo lot A6888B, Leo Pharma A/S, Ballerup, Denmark.

Example 1

Apixaban is a direct acting inhibitor of activated coagulation factor X (FXa). It is the active compound of the antithrombotic drug Eliquis, Bristol-Meyers Squibb. It is of clinical interest to measure apixaban in blood plasma in the range 50 to 1000 µg/L. To prepare suitable samples, small volumes of the stock solution of apixaban was added to normal plasma, the control plasma NKP, to give normal plasma with apixaban content in the range 0 to 1000 µg/L. These normal plasmas with apixaban, including the unadulterated normal plasma (NKP) and the same diluted 1:2 in 9 g/L NaCl (NKP 1:2) were all analyzed by Simple Simon PT at sample additions of 20 µL, 10 µL and 5 µL in 200 µL reagents, thus with three PT-methods with different sample content in the reaction mixtures, according to the invention. It was further relevant that all three PT-methods were calibrated, according to the invention, to show INR 1.000 for unadulterated NKP, and INR 1.357 for the NKP 1:2. All primary INR values, the results that appeared on the instrument screens (one instrument or reader was used for each PT-method), were therefore transformed to the corrected/calibrated INRc by the formula A*INRexp(B) where a and b were selected to given NKP and NKP 1:2 their desired values, 1.000 and 1.357, respectively. The INR-value of the NKP 1:2 was calculated by the formula of Lindahl et al for the INR of corresponding to PT-activity of 50% (half of the 100% that equates to INR 1.000). The data treatment is shown in Table 1. Above the INR calibrated columns (INRc) there is an upper number and a lower number, these are the above mentioned A and B, respectively.

In the above this is done in a less sophisticated way. A portion (56%) of the lesser INRc-difference is subtracted from the INRc-results of the 5 µL sample method, the result obviously closest to INRo. These simple INRo-estimates are surprisingly good, only the one at top apixaban content (1000 µg/L) is off by more than a tenth of an INR-unit.

Figure 2:
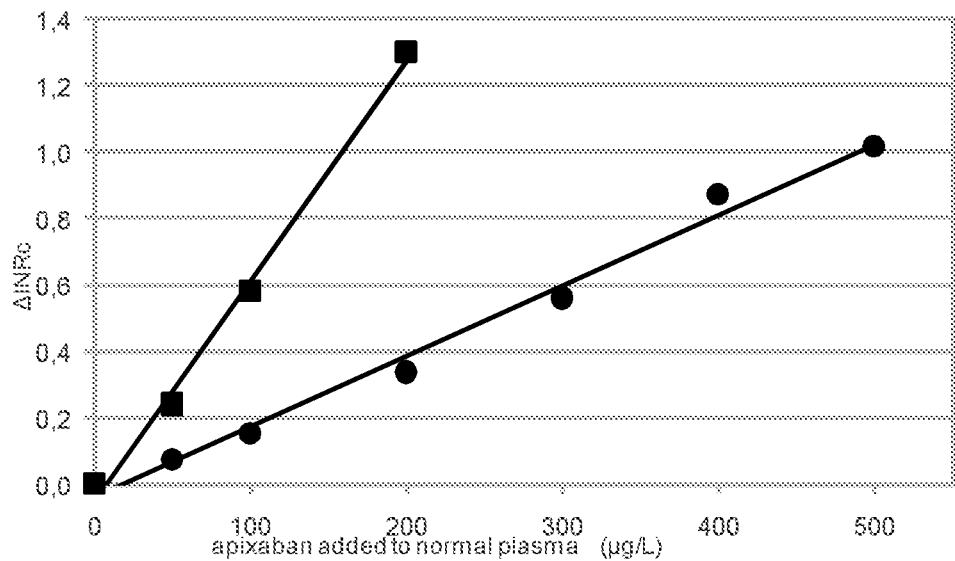
FIG. 2 is a magnification of a portion of the graph in FIG. 1.

FIGS. 1 and 2 show graphs in which the rate of increase in the measures of apixaban content increases with the content. However, for those many that appreciate/favors linear dose-response relationships, such relationships are here displayed by apixaban measures that are below one INR-unit as seen in the graph in FIG. 2, where FIG. 2 shows a magnification of a portion of the graph in FIG. 1.

The data treatment showed in FIGS. 1 and 2 could be confusing to those unfamiliar to ambient room temperature determination of INR. Instead of a primary INR-result which has been corrected for temperature effect by the computations by the instrument/reader, we could instead consider the PT in seconds. This is done to increase the clarity in describing the invention in spite of introducing an error due to the temperature not being strictly constant during the time period in which the assays were performed (temperatures varied from 22.3° C. to 24.2° C.). In spite of this bias the results are still good enough to be convincing, and explains more clearly because it allows a data-treatment familiar to all with knowledge in the art, i.e. computation of INR by dividing the PT (in seconds) by a normal PT and powering the ratio with a normalizing constant equivalent to the ISI.

In Table 2 the results of the assay on normal plasma (NKP) with added apixaban is shown, but the primary data

TABLE 1

| apixaban µg/L | INR 20 µL sample | INR 10 µL sample | INR 5 µL sample | 0.94 1.31 INRc 20 µL sample | 0.93 1.21 INRc 10 µL sample | 0.95 0.97 INRc 5 µL sample | ΔINR 20 µL − 5 µL | ΔINR 10 µL − 5 µL | 0.54 INRo |
|---|---|---|---|---|---|---|---|---|---|
| 1000 | 10.70 | 4.41 | 2.67 | 21.03 | 5.58 | 2.47 | 18.56 | 3.12 | 0.78 |
| 800 | 7.81 | 3.35 | 2.22 | 13.91 | 4.00 | 2.06 | 11.85 | 1.94 | 1.01 |
| 600 | 5.56 | 2.70 | 1.90 | 8.91 | 3.08 | 1.77 | 7.14 | 1.31 | 1.06 |
| 500 | 4.47 | 2.37 | 1.73 | 6.69 | 2.63 | 1.62 | 5.07 | 1.02 | 1.07 |
| 400 | 3.68 | 2.16 | 1.58 | 5.18 | 2.35 | 1.48 | 3.70 | 0.87 | 1.01 |
| 300 | 2.82 | 1.82 | 1.44 | 3.66 | 1.91 | 1.35 | 2.30 | 0.56 | 1.05 |
| 200 | 2.12 | 1.53 | 1.29 | 2.51 | 1.55 | 1.22 | 1.30 | 0.34 | 1.03 |
| 100 | 1.55 | 1.27 | 1.15 | 1.67 | 1.24 | 1.09 | 0.58 | 0.15 | 1.01 |
| 50 | 1.28 | 1.18 | 1.12 | 1.30 | 1.13 | 1.06 | 0.24 | 0.07 | 1.02 |
| 0 | 1.05 | 1.065 | 1.055 | 1.00 | 1.00 | 1.00 | 0.00 | 0.00 | 1.00 |
| NKP | 1.050 | 1.065 | 1.055 | 1.000 | 1.000 | 1.000 | | | |
| NKP 1:2 | 1.325 | 1.37 | 1.445 | 1.357 | 1.357 | 1.357 | | | |

Two measurements of the apixaban content of the normal plasma are shown, a more sensitive measure, the difference in INRc given by PT-methods with 20 µL sample and 5 µL sample, and a less sensitive measure, the INRc-difference between 10 µL and with 5 µL. The INRc-differences are here shown as absolute differences, but relative INRc-differences could equally well have been used. The INRc-differences are plotted against the apixaban content of the normal plasmas as shown in the graph in FIG. 1. The square symbols are the difference in INRc between the results of 20 µL method and the 5 µL method, and the round symbols the difference in INRc between the 10 µL method and the 5 µL.

It is pointed out that it is possibility to estimate the INR of the normal plasma in the absence of anticoagulant, INRo.

is here in PT, in seconds, and the data is converted into INRc by division with the PT of a normal plasma and subjecting the ratio to the power of an ISI, upper and lower number, respectively, shown above the INRc-columns. As deemed relevant the upper number is selected to make NKP 1:2 to show INRc 1.357.

In Table 2 data is biased by a temperature gradient running from 22.3° C. at the top to 24.2° C. at the bottom.— This, however, does little to disturb the general picture. The PT-methods used, ambient temperature Owrens methods, are more sensitive to inhibitors than others, still it is obvious, that a single of the selected PT-methods would not give much useful information at lower levels of apixaban.

TABLE 2

| apixaban µg/L | PT (s) 20 µL sample | PT (s) 10 µL sample | PT (s) 5 µL sample | 32.8 2.63 INRc 20 µL sample | 37.3 1.66 INRc 10 µL sample | 45.8 1.07 INRc 5 µL sample | ΔINRc 20 µL − 5 µL | ΔINRc 10 µL − 5 µL | 0.54 INRo |
|---|---|---|---|---|---|---|---|---|---|
| 1000 | 117.4 | 109.3 | 111.2 | 28.43 | 5.94 | 2.57 | 25.85 | 3.37 | 0.75 |
| 800 | 96.9 | 87.2 | 91.7 | 17.18 | 4.08 | 2.09 | 15.08 | 1.99 | 1.02 |
| 600 | 79.9 | 73.9 | 78.8 | 10.35 | 3.10 | 1.78 | 8.57 | 1.32 | 1.07 |
| 500 | 70.8 | 67.0 | 72.0 | 7.54 | 2.64 | 1.62 | 5.92 | 1.02 | 1.07 |
| 400 | 63.5 | 62.3 | 66.3 | 5.66 | 2.34 | 1.48 | 4.18 | 0.86 | 1.02 |
| 300 | 54.8 | 54.6 | 60.6 | 3.85 | 1.88 | 1.35 | 2.50 | 0.53 | 1.06 |
| 200 | 46.7 | 47.9 | 54.4 | 2.53 | 1.51 | 1.20 | 1.33 | 0.31 | 1.03 |
| 100 | 39.3 | 41.5 | 49.1 | 1.61 | 1.19 | 1.08 | 0.53 | 0.12 | 1.01 |
| 50 | 35.5 | 39.1 | 47.7 | 1.23 | 1.08 | 1.04 | 0.19 | 0.04 | 1.02 |
| 0 | 32.8 | 37.3 | 45.8 | 1.00 | 1.00 | 1.00 | 0.00 | 0.00 | 1.00 |
| NKP | 32.8 | 37.3 | 45.8 | 1.00 | 1.00 | 1.00 | | | |
| NKP 1:2 | 36.9 | 44.9 | 61.0 | 1.357 | 1.357 | 1.357 | | | |

Imagine that you employ the most apixaban sensitive method of the three methods, the one with 20 µL of sample, and you obtain a PT of 35.2 seconds. This is more than that of a normal plasma (NKP), 32.8 seconds, but is the increase in PT due to anticoagulants, or is it due to low content of coagulation factors (the PT of NKP 1:2 is 36.9 seconds)? How can you tell? Practice of the assay, performing two or more PT-determinations with PT-methods with different sample content in the reaction mixture gives a clearer picture. Since the methods, which are calibrated to show the same PT (here the same INR called INRc, the c for calibrated) varies for samples that lack the anticoagulants to be determined, there will be little or no difference, i.e. no significant difference, between the INRc-results for a sample with low coagulation factor content. In the present example it is known that the samples contain the anticoagulant apixaban because this has been added, and a difference in INRc-result appears. In the example there are three PT-methods used according to the invention, and there are three differences in INRc-results that can be examined (two of the three are shown in Table 2), and for the assay of normal plasma with 50 µg/L of apixaban, all three differences indicate the presence of anticoagulant. If the identity of the anticoagulant is known its content can be estimated. The INRc-differences are here shown as absolute differences, but relative INRc-differences could equally well have been used. Also the expected INRc for the sample in absence of inhibitor, INRo, can be estimated. Table 2 showing the PTs in seconds, clarifies the utility of practicing the invention. The results shown in Table 2 are expected to be near identical to those in Table 1, and they are in fairly good agreement. The differences noted for the samples with the highest apixaban content are blamed on the temperature effect. The temperature increased by about 2° C. while the experimental series was performed. The instruments has compensated for the effects of this temperature shift prior to reporting the INR values shown in Table 1. The PT values (clotting time in seconds) shown in Table 2, are, of course, not corrected for this temperature effect (PTs expressed in seconds are what they are). Hence the small differences in INRc shown in Table 1 and Table 2.

Figure 3:
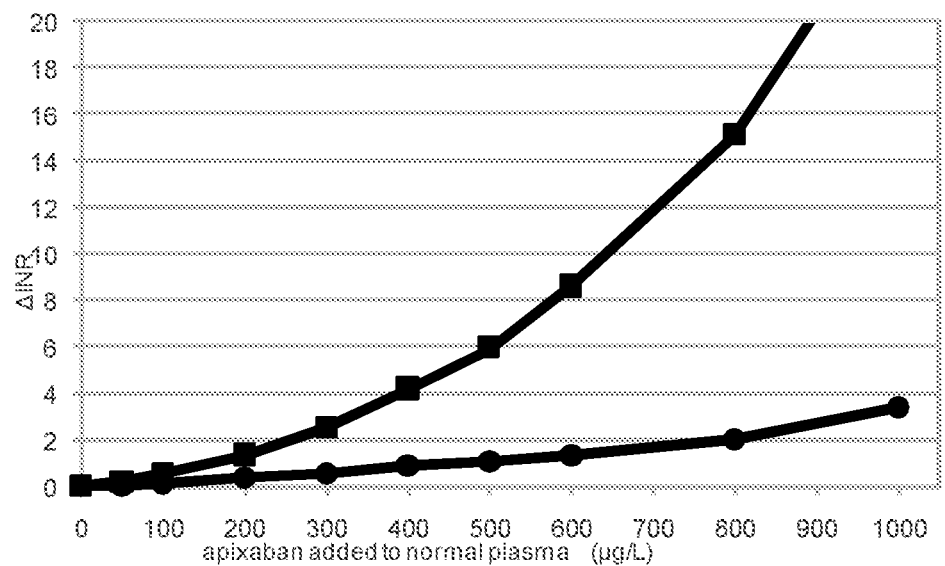
FIG. 3 is a graph showing apixaban content measured with the present assay in normal blood plasma (primary data: PT in seconds).
Figure 4:
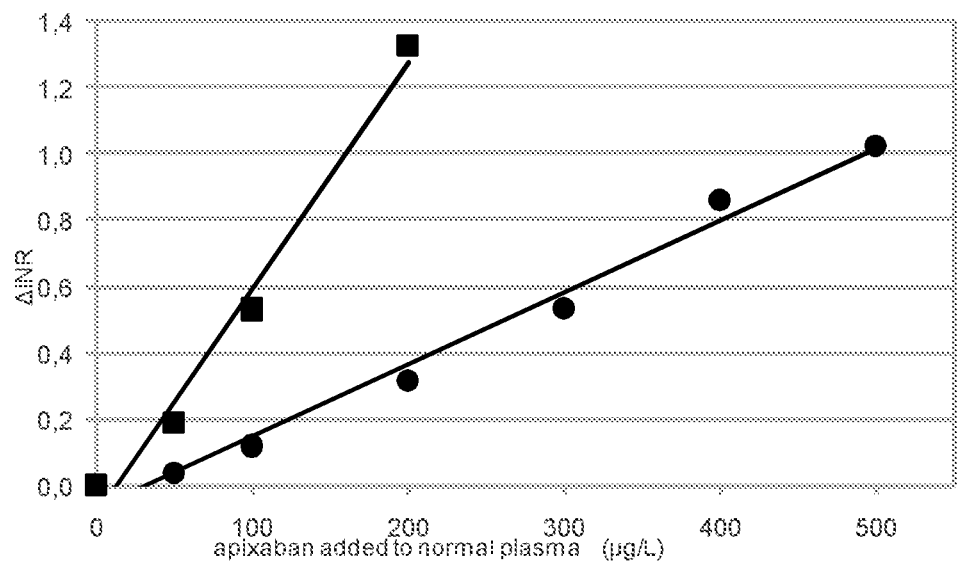
FIG. 4 is a magnification of a portion of the graph in FIG. 3.

In the graphs in FIGS. 3 and 4 the data from Table 2 has been inserted. INRc-differences are plotted against the apixaban content of the normal plasmas (difference in INRc given by PT-methods with 20 µL sample and 5 µL sample (squares), and INRc-difference between 10 µL and with 5 µL (dots)). The graph in FIG. 4 is a magnification of a portion of the graph in FIG. 3.

Example 2

Apixaban in the range 0 to 1000 µg/L was added to a normal citrated blood. These blood samples and a blood sample with an INR 2.3 were analyzed by Simple Simon PT using sample volumes of 20 µL, 10 µL and 5 µL in 200 µL reagents. The primary results in INR, and after relevant calibration, INRc, are displayed in Table 3:

TABLE 3

| apixaban µg/L | INR 20 µL bld | INR 10 µL bld | INR 5 µL bld | 0.87 0.96 INRc 20 µL bld | 0.93 1.10 INRc 10 µL bld | 1.01 1.15 INRc 5 µL bld | ΔINRc 20 µL − 5 µL | ΔINRc 10 µL − 5 µL | 1.5 INRo |
|---|---|---|---|---|---|---|---|---|---|
| 1000 | 8.76 | 3.50 | 2.21 | 6.94 | 3.69 | 2.51 | 4.43 | 1.16 | 0.74 |
| 714 | 6.06 | 2.78 | 1.87 | 4.88 | 2.86 | 2.08 | 2.80 | 0.78 | 0.91 |
| 500 | 4.58 | 2.27 | 1.66 | 3.73 | 2.29 | 1.81 | 1.92 | 0.48 | 1.09 |
| 250 | 2.61 | 1.64 | 1.32 | 2.18 | 1.60 | 1.39 | 0.79 | 0.21 | 1.07 |
| 125 | 1.75 | 1.32 | 1.13 | 1.49 | 1.26 | 1.16 | 0.32 | 0.10 | 1.02 |
| 63 | 1.41 | 1.19 | 1.04 | 1.21 | 1.12 | 1.06 | 0.15 | 0.06 | 0.96 |
| 0 | 1.16 | 1.06 | 0.00 | 1.00 | 1.00 | 1.00 | 0.00 | −0.01 | |
| N-blod 0.37 | 1.16 | 1.06 | 0.99 | 1.00 | 1.00 | 1.00 | 0.00 | −0.01 | |
| C-blod 2.3 | 2.76 | 2.27 | 2.05 | 2.30 | 2.30 | 2.30 | 0.00 | 0.00 | |

Figure 5:
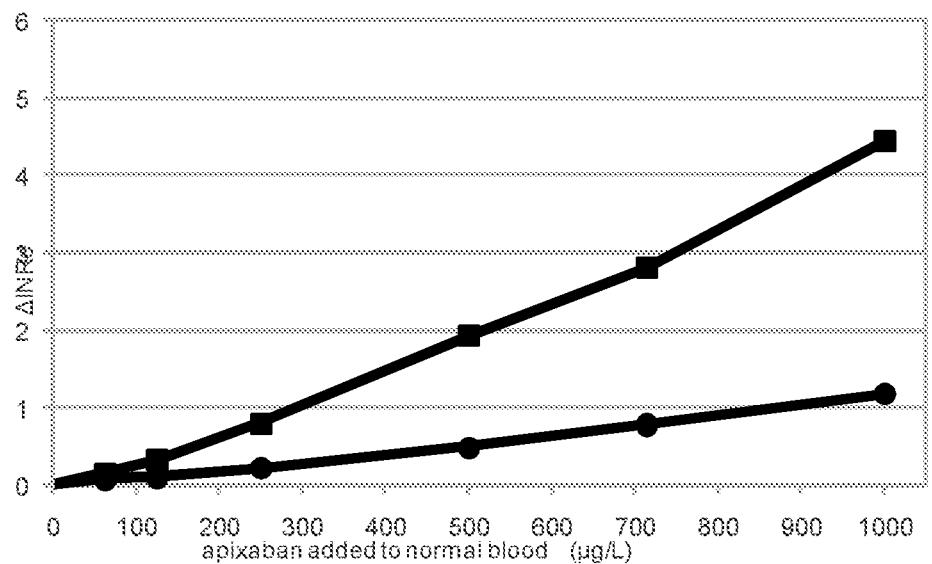
FIG. 5 is a graph showing apixaban content measured with the present assay in normal blood.
Figure 6:
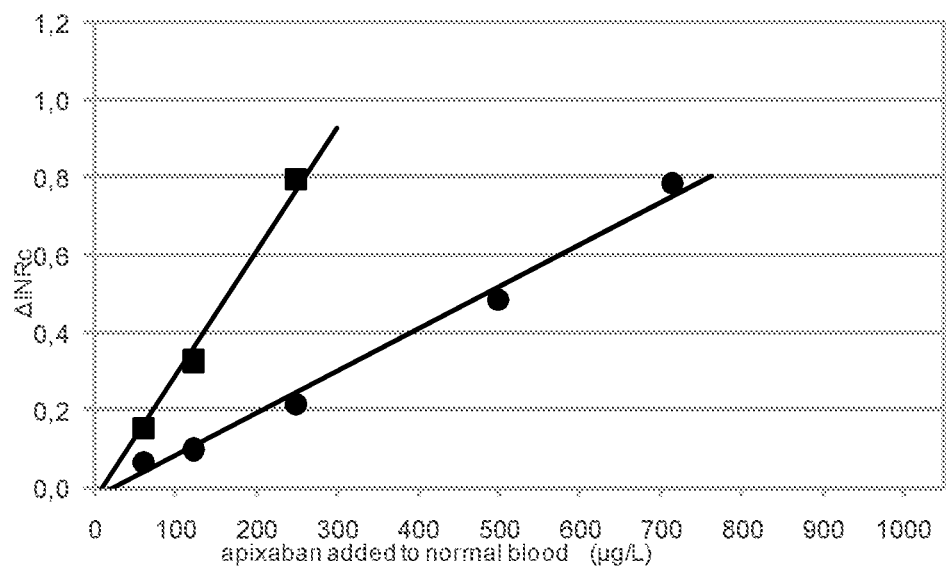
FIG. 6 is a magnification of a portion of the graph in FIG. 5

Here it was decided, for all three PT-methods, that the normal blood without addition of apixaban was to show INRc 1.00, and a citrated blood, reported by the central hospital laboratory to show INR 2.3 was here to show INRc 2.30. As in previous examples the absolute difference in INRc-results (alternatively relative difference may be used) are viewed as measures of anticoagulant content, here apixaban content, and two of the three possible such differences are plotted against the known apixaban content and displayed in FIGS. 5 and 6. The difference in INRc given by PT-methods with 20 μL sample and 5 μL sample is shown as squares and INRc-difference between 10 μL and with 5 μL as dots. The graph in FIG. 6 is a magnification of a portion of the graph in FIG. 5.

The dose-responses of the anticoagulant method of the invention show good positive dose-response characteristics over a range of apixaban in blood that is of clinical interest. The dose-response is again linear for differences in INRc of less than unity, see FIG. 6.

Example 3

Figure 7:
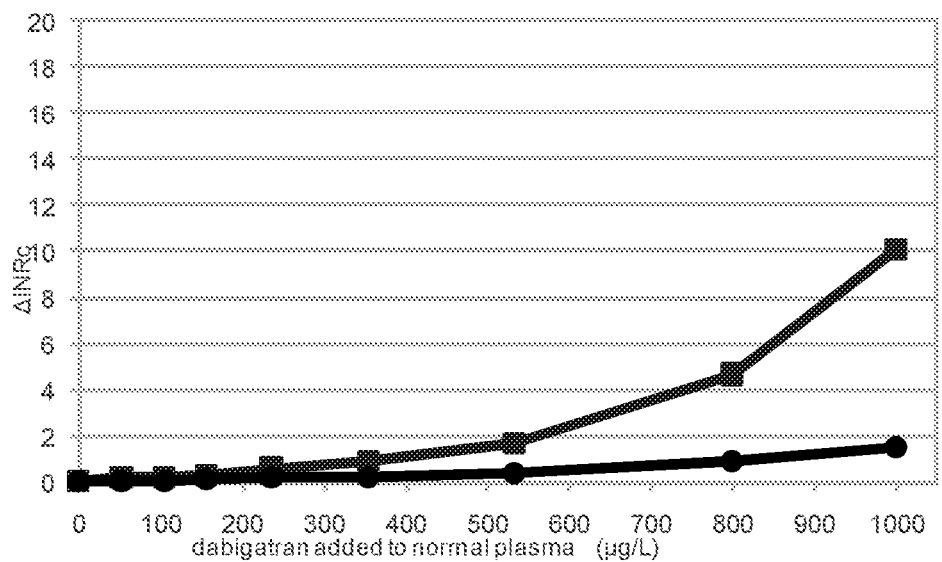
FIG. 7 is a graph showing dabigatran content measured with the present assay in normal blood.
Figure 8:
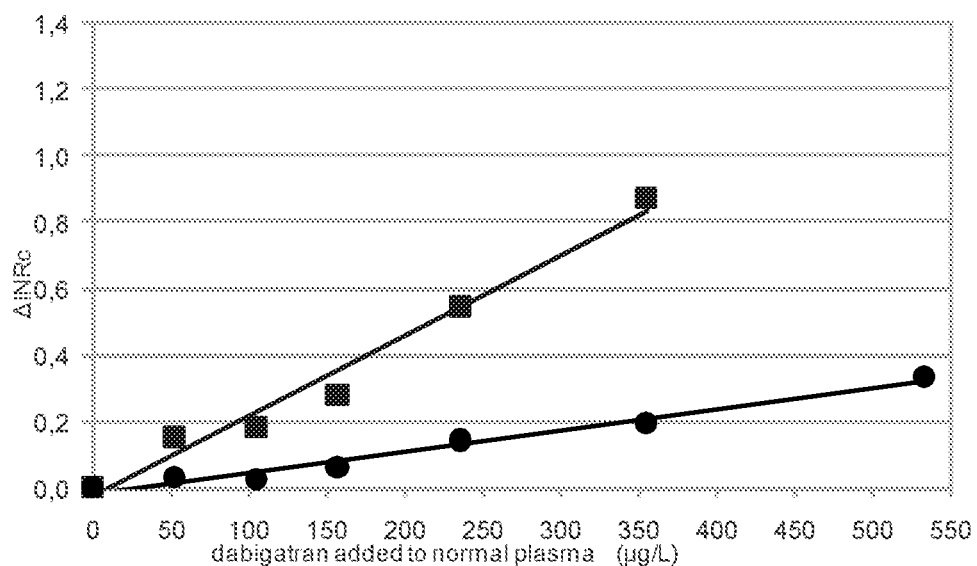
FIG. 8 is a magnification of a portion of the graph in FIG. 7.

Dabigatran is the active compound formed in vivo when the pharmaceutical preparation containing dabigatran-etexilate, Pradaxa, Boehringer-Ingelheim, is administered per os, i.e. orally. Clinical levels of interest range from 50 to 1000 μg/L in blood plasma. Such samples were created by adding small volumes of stock solution of dabigatran to normal blood plasma, NKP. Results and data-treatment, similar to that in Example 1 are shown in Table 4.

graph (see FIG. 8, a magnification of a portion of the graph in FIG. 7) reaches 0.5 at about 200 μg/L of dabigatran, whereas the same is reached at about 80 μg/L of apixaban, see FIG. 2, i.e. a more than twofold difference in sensitivity. Yet, dabigatran levels of 50 μg/L of dabigatran appear to be detectable. Not surprising, the assay to determine anticoagulants shows different sensitivities for different anticoagulants. In addition different sensitivities are expected with different reagents, and at different temperature at which the PT analyses are performed.

Example 4

Heparin is an anticoagulant that is difficult to reliably determine at point of care sites, such as at surgical wards. More convenient methods are wanted. In this the utility of the present assay to determine anticoagulants is exemplified below. The example is with unfractionated heparin, often used as antithrombotic agent in extensive surgery.

TABLE 4

| dabigatran μg/L | INR 20μL sample | INR 10μL sample | INR 5μL sample | 0.95 1.32 INRc 20μL sample | 0.94 1.12 INRc 10μL sample | 0.96 0.98 INRc 5μL sample | ΔINRc 20μL − 5μL | ΔINRc 10μL − 5μL | 1 INRo |
|---|---|---|---|---|---|---|---|---|---|
| 1000 | 7.03 | 3.55 | 2.53 | 12.47 | 3.89 | 2.39 | 10.08 | 1.51 | 0.88 |
| 800 | 4.22 | 2.50 | 1.81 | 6.36 | 2.62 | 1.72 | 4.64 | 0.91 | 0.81 |
| 533 | 2.38 | 1.70 | 1.44 | 2.98 | 1.70 | 1.37 | 1.61 | 0.33 | 1.04 |
| 355 | 1.82 | 1.44 | 1.28 | 2.09 | 1.41 | 1.22 | 0.87 | 0.19 | 1.03 |
| 236 | 1.53 | 1.30 | 1.17 | 1.67 | 1.26 | 1.12 | 0.55 | 0.14 | 0.98 |
| 157 | 1.31 | 1.19 | 1.13 | 1.36 | 1.14 | 1.08 | 0.28 | 0.05 | 1.02 |
| 105 | 1.22 | 1.13 | 1.10 | 1.24 | 1.07 | 1.05 | 0.18 | 0.02 | 1.03 |
| 52 | 1.16 | 1.09 | 1.05 | 1.16 | 1.03 | 1.01 | 0.15 | 0.03 | 0.98 |
| 0 | 1.04 | 1.06 | 1.05 | 1.00 | 1.00 | 1.00 | 0.00 | 0.00 | |
| NKP | 1.04 | 1.06 | 1.05 | 1.000 | 1.000 | 1.000 | 0.00 | 0.00 | |
| NKP 1:2 | 1.31 | 1.39 | 1.43 | 1.357 | 1.357 | 1.357 | 0.00 | 0.00 | |

In comparing Table 4 with Table 1 in Example 1, it appears that the displayed embodiment of the invention is less sensitive for dabigatran than for apixaban in plasma. The impression is strengthened when comparing the graphs in FIGS. 7 and 8, with the corresponding figures of Example 1.

The more sensitive INRc-difference (20 μL minus 5 μL, shown as squares in FIGS. 7 and 8) in the linear part of the Samples were prepared by adding small volumes of a stock solution of heparin to normal plasma, NKP. In the selected calibration INR 1.000 and INR 1.357 were assigned to NKP and NKP 1:2, respectively, which was the same relevant calibration as selected in Examples 1 and 3 above. Experimental details are the same as example 1 and 3, and the results and data-treatment are shown in Table 5.

TABLE 5

| NKP heparin U/ml | 20 μL sample | 10 μL sample | 5 μL sample | 0.95 1.32 INRc 20 μL sample | 0.94 1.12 INRc 10 μL sample | 0.96 0.98 INRc 5 μL sample | ΔINRc 20 μL − 5 μL | ΔINRc 10 μL − 5 μL | 0.43 INRc |
|---|---|---|---|---|---|---|---|---|---|
| 5 | 6.47 | 2.10 | 1.35 | 11.17 | 2.16 | 1.29 | 9.88 | 0.87 | 0.91 |
| 2.5 | 2.46 | 1.40 | 1.13 | 3.12 | 1.37 | 1.08 | 2.04 | 0.29 | 0.96 |
| 1.2 | 1.47 | 1.19 | 1.11 | 1.58 | 1.14 | 1.06 | 0.52 | 0.08 | 1.03 |
| 0.6 | 1.26 | 1.12 | 1.08 | 1.29 | 1.06 | 1.03 | 0.26 | 0.03 | 1.02 |
| 0 | 1.04 | 1.06 | 1.05 | 1.00 | 1.00 | 1.00 | 0.00 | 0.00 | 1.00 |
| NKP | 1.04 | 1.06 | 1.05 | 1.00 | 1.00 | 1.00 | | | |
| NKP 1:2 | 1.31 | 1.39 | 1.43 | 1.36 | 1.36 | 1.36 | | | |

Figure 9:
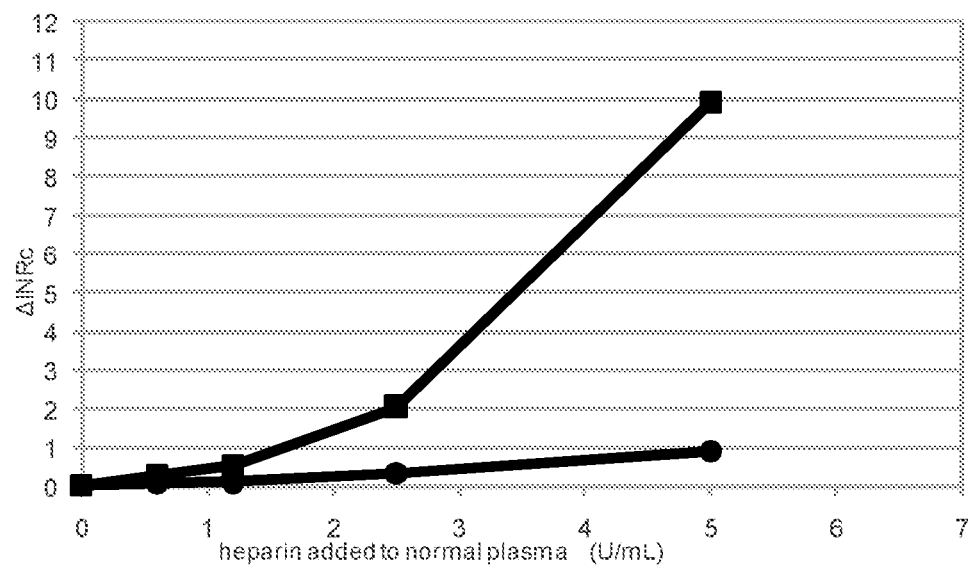
FIG. 9 is a graph showing heparin content measured with the present assay in normal blood plasma.
Figure 10:
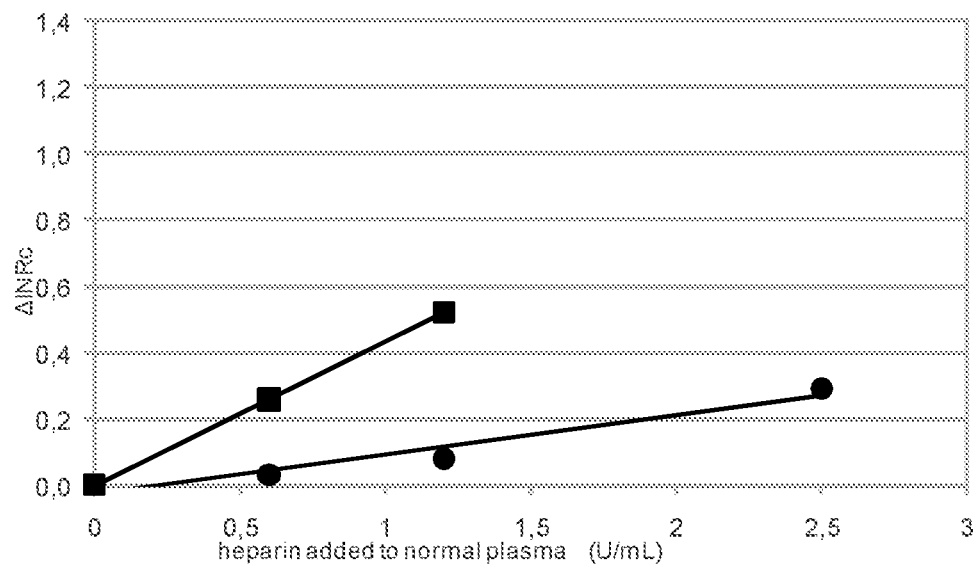
FIG. 10 is a magnification of a portion of the graph in FIG. 9.

Plotting the measure of anticoagulant content in the normal plasma, the absolute difference in INRc (alternatively relative difference may be used) for two of possible three differences against the heparin content gives the graphs in FIGS. 9 and 10. As seen from Table 5 and FIGS. 9 and 10, the heparin may be detected at about 0.2 U/mL and determined in the concentration range 0.2 to 5 U/mL, which is of clinical relevance.

Example 5

According to the present anticoagulant assay, two or more PT methods, of which one has a greater proportion of sample in the reaction mixture than another, are calibrated to show, as nearly as possible, the same PT for reference samples devoid of anticoagulants of interest, i.e. devoid of anticoagulants that can be determined by the assay. By definition, the PTs of the reference samples are known, either as an average for a group of reference samples, or individually.

In this example the reference samples are of two kinds; plasma samples from normal individuals (n=34) and plasma samples from patients treated with warfarin (n=30). The PT of the reference samples are known by reference analyses performed at the central laboratory of the University Hospital of Linköping, Sweden. The average reference PT of the normal individuals and the warfarin patients were 23.1 and 51.5 seconds, respectively.

The two PT methods of the present anticoagulant assay were one with 20 μL of sample added to 200 μL of PT-reagent (higher proportion of sample in the reaction mixture) and another with 5 μL of sample added to 200 μL of the same reagent (lower proportion of sample in the reaction mixture). These two methods showed average PT of 32.8 and 65.3 seconds, and 41.8 and 104.3 seconds for the reference samples of normal individuals and of warfarin patients, respectively. Both PT methods, the 20 μL-method and 5 μL-method, were then calibrated to show the same average PT (in synthetic seconds) as the reference method for both sets of reference samples. This was accomplished by constants A20 and B20, and A5 and B5 in transforming the PTs of the 20 μL-method and 5 μL-method, respectively, into the calibrated PT values (PTc) by the expression PTc=A*PTexpB. The differences in PTc for each sample by the two methods, expressed either as a ratio (PT20c/PT5c) or in absolute terms (PT20c minus PT5c), were calculated and plotted against the average PTc of the two methods, see FIGS. 11 and 12.

Two of the reference samples in the patient group (marked with X in the graphs) showed differences that were statistically outside of a normal distribution of differences defined by the other reference samples (squares). These deviant samples may contain the anticoagulant heparin, an anticoagulant which can be determined by the present anticoagulant assay (see Example 4), and which is used to treat some hospitalized warfarin patients while warfarin treatment is in effect.

Figure 11:
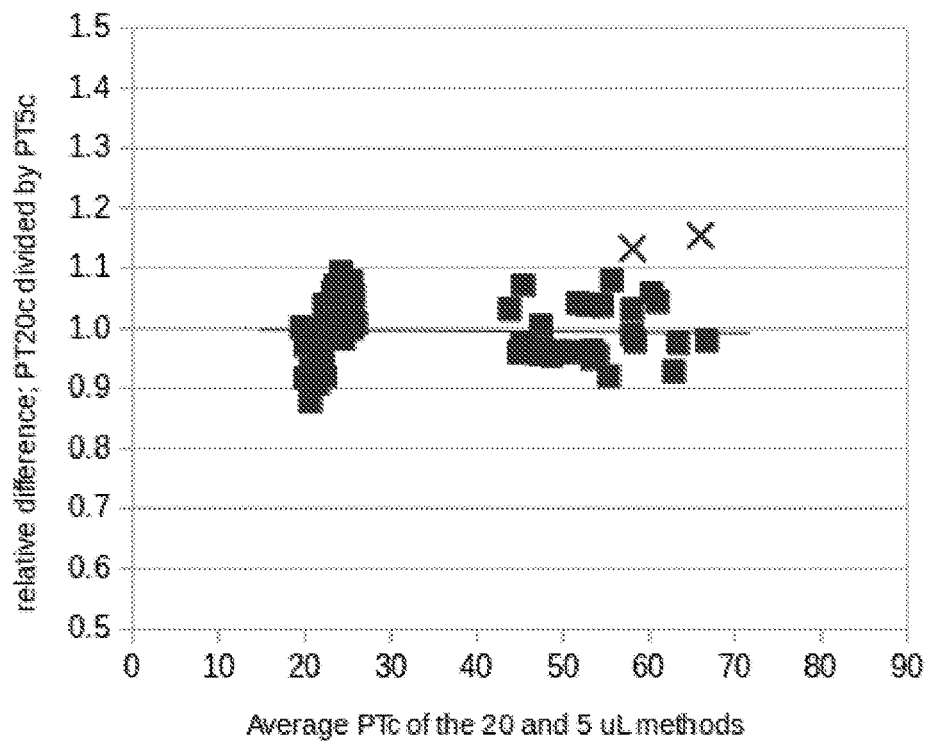
FIG. 11 is a graph showing relative difference of PT20c/PT5c against average PTc for 5 µl and 20 µl methods when measuring reference samples from normal individuals and patients treated with warfarin.
Figure 12:
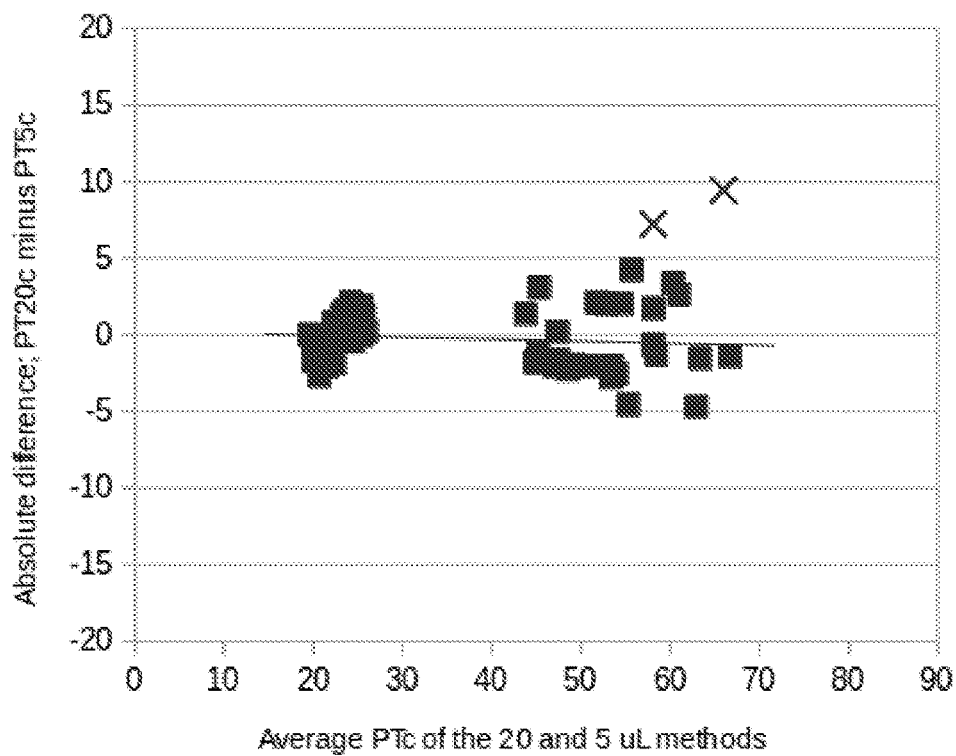
FIG. 12 is a graph showing absolute difference of PT20c-PT5c against average PTc for 5 µl and 20 µl methods when measuring reference samples from normal individuals and patients treated with warfarin.

The use of the relative difference, FIG. 11, or absolute difference, FIG. 12, between the calibrated PT results of the two PT methods of the assay is an option. Here the relative difference, expressed as the ratio, displays an advantage in that the standard deviation is about the same in the normal PT range as in the elevated PT range, 0.054 and 0.044, respectively. The PTc ratio of the patient samples suspected of containing heparin displayed positive deviations from the average by 3.0 and 4.5 times the standard deviation defined by the other 28 patient samples. Statistically, the two deviants are unlikely, p<0.05, to be part of a distribution of PTc ratios defined by the other patient samples.

The same experimental set up used to analyze the 34 reference plasmas of normal individuals and the 30 reference plasmas of warfarin patients was also used to analyze plasma samples (n=13) from patients undergoing treatment with dabigatran (a thrombin inhibiting NOAC), or about to start on such treatment. The 13 patient plasma samples were from the Department of Acute Internal Medicine of the University Hospital of Linköping, Sweden.

Figure 13:
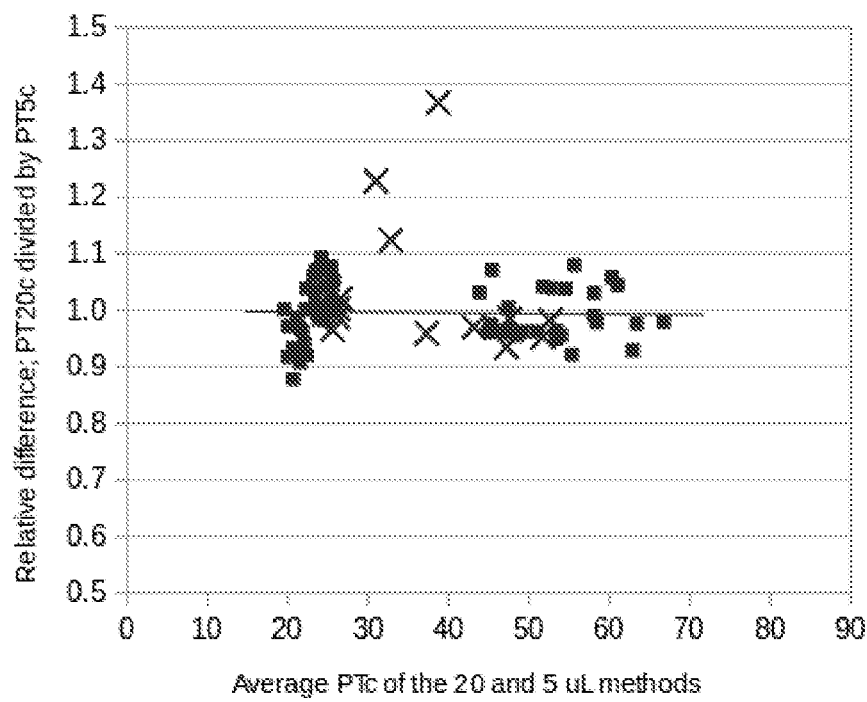
FIG. 13 is a graph showing relative difference of PT20c/PT5c against average PTc for 5 µl and 20 µl methods when measuring reference samples from normal individuals and patients treated with warfarin and samples from patients treated with dabigatran.
Figure 14:
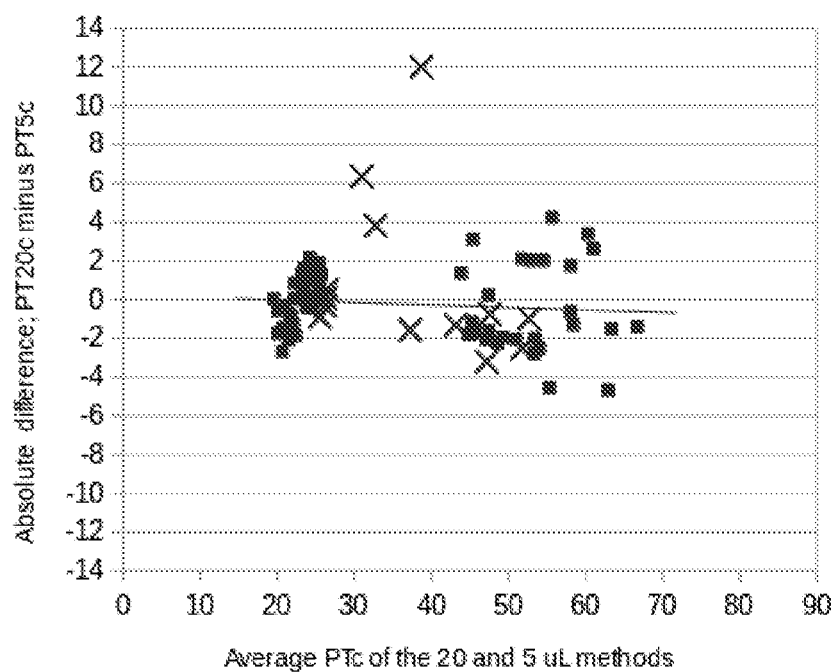
FIG. 14 is a graph showing absolute difference of PT20c-PT5c against average PTc for 5 µl and 20 µl methods when measuring reference samples from normal individuals and patients treated with warfarin and samples from patients treated with dabigatran.

The differences in PT20c and PT5c for the patient plasmas (marked with X), expressed either as ratio or in absolute numbers, were introduced into the plots of the reference samples (marked with squares) as seen in FIGS. 13 and 14, respectively.

Three of the NOAC patients showed PTc differences that were elevated outside of the normal distribution defined by the reference samples. According to an established method of determining dabigatran, the diluted thrombin time (dTT) method, the three samples that showed elevated PTc difference contained 172, 224 and 350 μg/L of dabigatran, respectively. The other 10 plasma samples from NOAC patients, none of which showed elevated PTc-difference, all contained <30 μg/L of dabigatran according to the dTT method.

Interestingly, there were several samples among the 13 dabigatran patient samples that showed elevated PTc values with both the 20 μL-method and the 5 μL-method, but without significant difference between the methods. The findings are consistent with effects of warfarin treatment, but not of dabigatran treatment. The disclosed anticoagulant assay is thus capable of making the distinction. The assay is thus capable of estimating both the PT and the NOAC (anticoagulant) content of a sample. The non-content of dabigatran, <30 μg/L, of the samples was displayed by an insignificant PTc-difference. The finding was confirmed by established method (dTT) for dabigatran determination. All 10 of the 13 samples with insignificant PTc difference by the present assay contained <30 μg/L according to dTT determination.

In practicing the anticoagulant assay, both PT methods, the one with high and the one with low sample content in the reaction mixture, are calibrated to numerically show reference levels of PT. Here, in this example, the PT results of the two methods of the assay were calibrated to show what is referred to as synthetic time, not real seconds, but numerical values that mirror the PT, in seconds, of a reference method. If the PT of the reference samples is expressed in INR, then the methods of the invention are calibrated to give, as closely as possible, the same INR as these reference samples. If the reference samples have their reference PT expressed in percent of normal PT, then these values are used in the calibration.

Example 6

As in above example 5, the two or more PT methods of the present anticoagulant assay, one with higher sample content in the reaction mixture than another, are both calibrated to show reference PT results with two sets of reference samples; 34 plasmas from normal individuals and 30 plasma from patients on warfarin treatment.

All reference PT values were determined by the central laboratory of the University Hospital of Linköping, Sweden. As in Example 5A, the two PT methods were one with 20 μL of sample added to 200 μL of PT-reagent and the other with 5 μL added to 200 μL of the same PT reagent. The non-calibrated PT results are referred to as PT20 and PT5, and calibrated PT results are referred to as PT20c and PT5c, respectively.

Also analyzed by the two PT methods were plasma samples (n=20) from patients on treatment with dabigatran at the Department of Acute Internal Medicine of the University Hospital of Linköping, Sweden. All of these 20 plasma samples had dabigatran levels above 34 μg/L according to an established dTT method mentioned also in Example 5.

Figure 15:
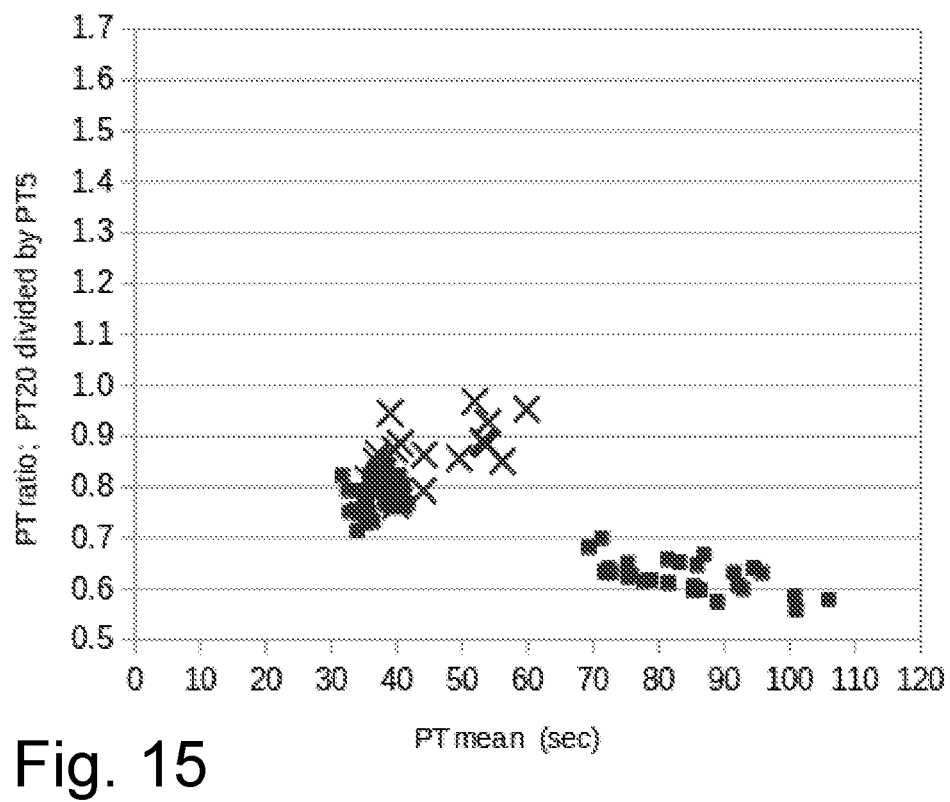
FIG. 15 is a graph showing relative non-calibrated differences of PT20/PT5 against average PT for 5 µl and 20 µl methods when measuring reference samples from normal individuals and patients treated with warfarin and samples from patients treated with dabigatran
Figure 16:
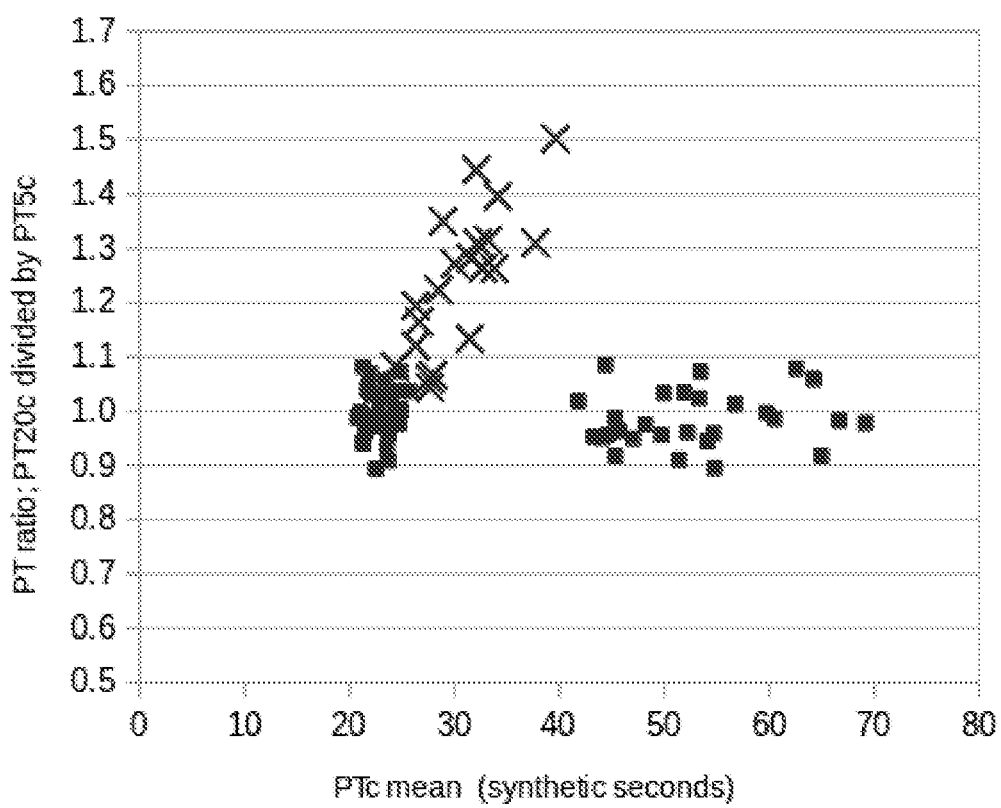
FIG. 16 is a graph showing relative calibrated differences of PT20c/PT5c against average calibrated PT for 5 µl and 20 µl methods when measuring reference samples from normal individuals and patients treated with warfarin and samples from patients treated with dabigatran

In FIGS. 15 and 16, before and after calibration, respectively, the difference between the two PT-results of the assay, expressed as ratios, are plotted against the mean of the two PT-results. In the figures, squares show the results with the reference samples, and Xs those of the NOAC (dabigatran) samples.

Prior to calibration, FIG. 15, the normal reference samples show a mean PT of about 35 seconds, and the warfarin patient reference samples mean PT ranging from about 65 to 110 seconds. After calibration, FIG. 16, the mean PT (mean PTc) of the normal reference samples is 23.1—not real seconds but synthetic ones—and the mean PTc of the warfarin patient reference samples range from about 40 to 70. After calibration these averages and ranges are, of course, very nearly the same as those obtained by the reference method, i.e. they mirror the reference values. In comparing FIG. 15 with FIG. 16, it is evident that calibration results in decisive improvements of the present anticoagulant assay. Straight forward statistical analysis show that about 80% of the clinical dabigatran samples, see FIG. 16, have detectable levels of anticoagulant (PTc ratios higher than mean plus 2*SD for the normal references samples). Prior to calibration, this was only 70%, see FIG. 15. More sophisticated, less intuitive, statistical analysis needs to be devised if calibration is not performed. After calibration the dabigatran samples show a PT difference (PTc difference) of a wider range, better suited for quantitative NOAC-determination. Not least important is the logic of the assay as conceived by an operator. After calibration, the one PT method with the higher proportion of sample in the reaction mixture will show higher PT values for samples with anticoagulants than the PT method with lower proportion—if there are no detectable levels of anticoagulants in the samples, the two PT methods will, of course, show about the same. Without calibration there is no such straight forward logic.

The two PT methods of the anticoagulant assay can be calibrated to show the reference values of the reference samples regardless of how the reference values are expressed. The reference values can, as in this example, be expressed in PT (seconds), or they can be expressed in INR or as fraction of normal activity. Calibration is in all cases possible and advantageous.

Example 7

Example 5 and 6 demonstrated a need to increase the sensitivity of the anticoagulant assay used, as only about 80% of the clinical samples with levels of dabigatran higher than 30 μg/L (according to established dabigatran methodology (dTT)) displayed anticoagulant levels above the detection limit by the assay, see FIG. 16 (note that the detection limit is practically along the horizontal line of 1.1).

The present example describes experiments performed with the aim to improve the sensitivity of the assay. Table 6 displays data from experiments where the PT liquid reagent (lot P161), contained various levels of added $CaCl_2$; either 4, 8, 16 or 32 mM. With each reagent three samples were analyzed by the two PT methods of the anticoagulant assay, the 20 μL-method and the 5 μL-method. Two of the samples were reference samples, the control plasmas NKP and ZAP, with established INR values of 1.00 and 2.50, respectively. The third sample was the NKP to which a small volume of stock solution of apixaban had been added to give an apixaban concentration of 500 μg/L. The results with each reagent were then calibrated to show INRc of 1.00 for the NKP and INRc of 2.50 for the ZAP. The NKP with 500 μg/L apixaban (NKP+500) then showed various INR20c and INR5c results. The difference, expressed as the ratio, INR20c/INR5c, was computed for each reagent, and is displayed in Table 6 in the column next to the far right.

To obtain a measure of sensitivity, the detection limit was estimated from the ratio INR20c/INR5c that was observed for the NKP+500 sample. This estimate was made under assumptions that i) the SD for the ratios of normal reference plasmas was 0.052 for all reagents (this value was obtained from the data in Example 6, and that ii) the ratio minus one increases from zero in proportion to the dabigatran level. Under these assumptions the detection limit for each reagent was computed as the dabigatran level at which the ratio reaches one plus 0.104 (2*SD). The computed detection limits are displayed in the far right column of Table 6.

The highest detection limit (lowest sensitivity), about 94 μg/L, was obtained with a reagent containing 4 mM of $CaCl_2$. For a reagent containing 8 mM of $CaCl_2$ the sensitivity was higher and the detection limit about 70 μg/L, and for a reagent with 16 mM $CaCl_2$ the sensitivity was still higher with a detection limit of 38 μg/L. A higher reagent content of $CaCl_2$ (24 and 32 mM) did not further increase the sensitivity and the detection limit remained at about the same level as with 16 mM CaCl2 in the reagent.

TABLE 6

| reagent ID | added Ca2+ (mM) | 20 uL-method NKP INR20c | 5 uL-method NKP INR5c | 20 uL-method ZAP INR20c | 5 uL-method ZAP INR5c | 20 uL-method NKP + 500 INR20c | 5 uL-method NKP + 500 INR5c | ratio INR20c/ INR5c | apixaban detection limit ug/L |
|---|---|---|---|---|---|---|---|---|---|
| P161 with zero Ca2+ | 4 | 1.00 | 1.00 | 2.50 | 2.50 | 1.83 | 1.18 | 1.55 | 94 |
| P161 with zero Ca2+ | 8 | 1.00 | 1.00 | 2.50 | 2.50 | 2.15 | 1.23 | 1.75 | 70 |
| P161 with zero Ca2+ | 16 | 1.00 | 1.00 | 2.50 | 2.50 | 3.15 | 1.33 | 2.37 | 38 |
| P161 with zero Ca2+ | 24 | 1.00 | 1.00 | 2.50 | 2.50 | 3.30 | 1.41 | 2.34 | 39 |
| P161 with zero Ca2+ | 32 | 1.00 | 1.00 | 2.50 | 2.50 | 3.38 | 1.49 | 2.27 | 41 |

Table 6 shows that a content of ionized calcium in the PT reagent in the range of about 10 to 50 mM results in increased sensitivity of the present anticoagulant assay. This is manifested as decreased detection limit. The level of ionized calcium in the reaction mixture is, because the reagent is only marginally diluted by the addition of sample, about the same as in the PT-reagent (diluted by about 10% in a 20 μL-method and by about 3% in a 5 μL-method). The results are surprising and unexpected since the level of ionized calcium is typically about 8 mM in the reaction mixture of standard PT-methods. This level is typically reached by addition of the soluble calcium salt $CaCl_2$ to the PT-reagent, but other sources of calcium ions are possible including calcium hydroxide, calcium lactate and other soluble calcium salts comprising non-disturbing anions. Even addition of metallic calcium is possible, although less practical.

An increase in ionized calcium concentration in the PT reaction mixture resulted in a progressive increase in the time needed to reach the coagulation point, the clotting time. For the 5 μL-method and the NKP sample (INR 1.00), the clotting time was 42.1, 47.4, 52.5, 70.1 and 82.1 seconds for calcium ion contents of about 4, 8, 16, 24 and 32 mM, respectively, in the reaction mixture. An increase in ionized calcium levels above that needed for an advantageous increase of the sensitivity of the assay is, because of the increased clotting time, perceived as disadvantageous. Because of this, a preferred ionized calcium ion concentration level is in the range of between 10 and 30 mM, or even within the range of between 10 and 24 mM.

In the coagulation reactions, ionized magnesium can often replace the functions of ionized calcium. This could also here be the case. The limits of ionized calcium levels stated could therefore be viewed as limits for the sum of ionized calcium levels and ionized magnesium levels.

In additional experiments aimed at increasing the sensitivity of the anticoagulant assay, the NaCl levels were increased in the PT reagent to levels that made the PT reagent hypertonic (higher osmotic pressure than that of blood plasma and other physiological solutions), hence, also made the reaction mixture hypertonic. This increased the sensitivity of the anticoagulant assay. Increase in anticoagulant assay sensitivity by increased osmolarity is also limited in scope because the clotting times may become excessively long if the NaCl levels are too high. In practice, to increase the sensitivity of the anticoagulant assay, the osmolarity of the reaction mixture may be increased to be within the range of 0.3 to 0.5 Osm/kg, or be even more limited to be within the range of 0.3 and 0.4 Osm/kg. Typically, the osmolarity of reaction mixtures of PT methods are quite close to physiological 0.308 Osm/kg, the same as a 0.154 M NaCl solution.

It is conceivable, that a combination of the measures described above which increase the sensitivity of the anticoagulant assay can be combined to give the most advantageous high sensitivity. The reaction mixture may be hypertonic by addition of NaCl to the range between 0.3 to 0.4 Osm/kg and also have levels of ionized calcium in the range 12 to 30 mM.

The invention claimed is:

1. An assay to determine anticoagulants expected to be present in a blood or blood plasma sample, wherein the anticoagulants are direct acting inhibitors of activated coagulation factors IIa and Xa selected from the group consisting of diabigatran, apixaban, rivaroxaban, and hirudin, or indirect acting inhibitors of activated coagulation factors IIa and Xa selected from the group consisting of fractionated heparins and unfractionated heparins, wherein the direct acting inhibitors of activated coagulation factors IIa and Xa are detected from 38 to 1000 μg/L and indirect acting inhibitors of activated coagulation factors IIa and Xa are detected from 0.2 to 5 U/ml, wherein said assay comprises analyses with at least two Owren-type prothrombine time (PT) methods, the assay comprising the steps of:
  a. measuring a first PT result expressed in INR, synthetic time-like units, or ratios of such, in a first reaction mixture comprising a first volume of blood or blood plasma diluted in a first volume of a liquid reagent comprising thromboplastin, fibrinogen, and coagulation factor V with a first Owren-type PT method using a first calibration;
  b. measuring a second PT result expressed in INR, synthetic time-like units, or ratios of such, in a second reaction mixture comprising a second volume of said blood or blood plasma diluted in a second volume of said liquid reagent with a second Owren-type PT method using a second calibration, wherein the concentration of blood or blood plasma in the second reaction mixture differs from the concentration of blood or blood plasma in the first reaction mixture,
  wherein said first and second calibrations give the same or approximately the same PT result when used in the first and second Owren-type PT methods to analyze reference blood or blood plasma which lack the anticoagulants; and
  wherein the assay further comprises the step of:
  c. calculating a difference in the first and second PT results from the measurements in step a) and b), wherein if said difference is:
    1. more than a predetermined value it is indicative of a presence of the anticoagulants in the blood or blood plasma sample; or
    2. less than the predetermined value it is indicative of an absence of the anticoagulants above a detectable level in the blood or blood plasma sample.

2. The assay according to claim 1, wherein if the difference calculated in step c) is more than the predetermined value and the anticoagulant is known, a concentration of the anticoagulant in said blood or blood plasma sample is computable.

3. The assay according to claim 1, wherein if the difference calculated in step c) is less than the predetermined value and the anticoagulant is known, a level above which the anticoagulant is not present in said blood or blood plasma sample is assignable.

4. The assay according to claim 1, wherein if the difference calculated in step c) is more than the predetermined value, an estimated Owren-type PT of the blood or blood plasma sample in the absence of anticoagulants is computable.

5. The assay according to claim 1, wherein the Owren-type PT analyses are performed at a temperature in the range of 17° C. to 45° C.

6. The assay according to claim 1, wherein the Owren-type PT analyses are performed at a temperature in the range of 18° C. to 30° C.

7. The assay according to claim 1, wherein the Owren-type PT analyses are performed at a temperature in the range of 21° C. to 30° C.

8. The assay according to claim 1, wherein the Owren-type PT analyses are performed at a temperature in the range of 25° C. to 30° C.

9. The assay according to claim 1, wherein the first volume of the liquid reagent in the first reaction mixture is equal to the second volume of the liquid reagent in the second reaction mixture.

10. The assay according to claim 1, wherein the first and second volumes of blood or blood plasma are in the range of 1 to 20 µL.

11. The assay according to claim 1, wherein the first and second volumes of blood or blood plasma are added to the liquid reagent with an end-to-end capillary.

12. The assay according to claim 1, wherein a ratio between the first and second volumes of blood or blood plasma and the volume of liquid reagent in the reaction mixture is 1:2 to 1:200, 1:5 to 1:100 or 1:10 to 1:50.

13. The assay according to claim 1, wherein a concentration of blood or blood plasma in the first reaction mixture is about 1.5 to 100 times, 1.5 to 50 times, 1.5 to 25 times, 1.5 to 10 times or 1.5 to 5 times higher than the concentration of blood or blood plasma in the second reaction mixture.

14. The assay according to claim 1, wherein the first and second reaction mixtures comprise a final concentration of calcium ions in the range of 10 to 50 mM, in the range of 10 to 30 mM, or in the range of 10 to 24 mM.

15. The assay according to claim 1, wherein the osmolarity of the first and second reaction mixtures is about 0.3 to 0.5 Osm/kg, or about 0.3 to 0.4 Osm/kg.

* * * * *